US012232983B2

(12) United States Patent
McLaughlin et al.

(10) Patent No.: US 12,232,983 B2
(45) Date of Patent: *Feb. 25, 2025

(54) VERTEBRAL IMPLANTS AND ATTACHMENT ASSEMBLIES

(71) Applicant: GLOBUS MEDICAL, INC., Audubon, PA (US)

(72) Inventors: Colm McLaughlin, Glenside, PA (US); Noah Hansell, King of Prussia, PA (US); Jeffrey D. Gordon, Phoenixville, PA (US); Mark Weiman, Downingtown, PA (US); George Howard, Green Lane, PA (US); Suresh Chintakunta, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,126

(22) Filed: Apr. 19, 2023

(65) Prior Publication Data

US 2023/0248540 A1 Aug. 10, 2023

Related U.S. Application Data

(63) Continuation of application No. 17/070,256, filed on Oct. 14, 2020, now Pat. No. 11,690,735, which is a
(Continued)

(51) Int. Cl.
*A61F 2/46* (2006.01)
*A61B 17/70* (2006.01)
(Continued)

(52) U.S. Cl.
CPC ............ *A61F 2/4637* (2013.01); *A61B 17/70* (2013.01); *A61F 2/44* (2013.01); *A61F 2/4455* (2013.01); *A61F 2/4465* (2013.01); *A61F 2/4611* (2013.01); *A61F 2002/30383* (2013.01); *A61F 2002/30387* (2013.01);
(Continued)

(58) Field of Classification Search
CPC .............. A61B 17/025; A61B 17/8004; A61B 17/8866; A61B 2017/0256; A61B 2017/681; A61F 2/4455; A61F 2/4611; A61F 2002/443
See application file for complete search history.

(56) References Cited

U.S. PATENT DOCUMENTS 6,176,881 B1 1/2001 Shar et al.
6,524,341 B2 2/2003 Lang et al.
(Continued)

*Primary Examiner* — Anu Ramana

(57) ABSTRACT

A prosthetic implant for engagement between first and second vertebrae. The implant includes a first plate configured for attachment to the first vertebrae and defining a first interbody connection member and a second plate configured for attachment to the second vertebrae and defining a second interbody connection member. An interbody component includes a body with a first end defining a first plate connection member configured for connection to the first interbody connection member and a second end defining a second plate connection member configured for connection to the second interbody connection member. A method of inserting the implant is also provided.

18 Claims, 21 Drawing Sheets

Related U.S. Application Data continuation of application No. 15/178,814, filed on Jun. 10, 2016, now Pat. No. 10,842,651.

(51) Int. Cl.
*A61F 2/44* (2006.01)
*A61F 2/30* (2006.01)

(52) U.S. Cl.
CPC .......... *A61F 2002/30505* (2013.01); *A61F 2002/30507* (2013.01); *A61F 2002/30556* (2013.01); *A61F 2002/30578* (2013.01); *A61F 2002/30593* (2013.01); *A61F 2002/4622* (2013.01); *A61F 2220/0033* (2013.01); *A61F 2220/0041* (2013.01)

(56) References Cited

U.S. PATENT DOCUMENTS

| | | | |
|---|---|---|---|
| 6,730,088 B2 | 5/2004 | Yeh | |
| 6,852,129 B2 * | 2/2005 | Gerbec | A61F 2/4637 623/17.15 |
| 6,866,682 B1 | 3/2005 | An et al. | |
| 6,899,734 B2 | 5/2005 | Castro et al. | |
| 6,908,485 B2 | 6/2005 | Crozet et al. | |
| 6,929,662 B1 | 8/2005 | Messerli et al. | |
| 7,156,874 B2 | 1/2007 | Paponneau et al. | |
| 7,303,584 B2 | 12/2007 | Castro et al. | |
| 7,311,733 B2 | 12/2007 | Metz-Stavenhagen | |
| 7,544,208 B1 | 6/2009 | Mueller et al. | |
| 7,575,601 B2 | 8/2009 | Dickson | |
| 7,648,529 B2 | 1/2010 | An et al. | |
| 7,758,648 B2 | 7/2010 | Castleman et al. | |
| 7,819,920 B2 | 10/2010 | Assaker | |
| 7,879,096 B2 | 2/2011 | Dickson et al. | |
| 7,909,870 B2 * | 3/2011 | Kraus | A61F 2/4611 623/17.11 |
| 7,914,581 B2 | 3/2011 | Dickson et al. | |
| 8,034,111 B2 | 10/2011 | Hsu et al. | |
| 8,057,545 B2 | 11/2011 | Hughes et al. | |
| 8,062,366 B2 * | 11/2011 | Melkent | A61F 2/44 623/17.11 |
| 8,182,535 B2 | 5/2012 | Kraus | |
| 8,197,546 B2 | 6/2012 | Doubler et al. | |
| 8,252,054 B2 * | 8/2012 | Greenhalgh | A61F 2/44 623/17.11 |
| 8,268,004 B2 | 9/2012 | Castleman et al. | |
| 8,282,683 B2 | 10/2012 | McLaughlin et al. | |
| 8,353,961 B2 | 1/2013 | McClintock et al. | |
| 8,366,779 B2 | 2/2013 | Dickson et al. | |
| 8,372,151 B2 | 2/2013 | Hsu et al. | |
| 8,568,482 B2 * | 10/2013 | Kraus | A61F 2/4611 623/17.15 |
| 8,585,763 B2 | 11/2013 | Olevsky et al. | |
| 8,591,585 B2 | 11/2013 | McLaughlin | |
| 8,657,882 B2 | 2/2014 | Bonin, Jr. | |
| 8,663,330 B2 | 3/2014 | McClintock et al. | |
| 8,721,723 B2 | 5/2014 | Hansell et al. | |
| 8,870,880 B2 | 10/2014 | Himmelberger | |
| 8,882,840 B2 | 11/2014 | McClintock et al. | |
| 9,009,927 B2 | 4/2015 | Rigollet et al. | |
| 9,173,747 B2 | 11/2015 | Hansell et al. | |
| 9,180,018 B2 | 11/2015 | Hansell et al. | |
| 9,259,323 B2 * | 2/2016 | Castro | A61F 2/447 |
| 9,271,842 B2 | 3/2016 | Davenport et al. | |
| 9,301,850 B2 | 4/2016 | McLaughlin et al. | |
| 9,844,446 B2 * | 12/2017 | McLaughlin | A61F 2/4611 |
| 10,004,606 B2 * | 6/2018 | Hirschl | A61F 2/442 |
| 2008/0167720 A1 | 7/2008 | Melkent | |
| 2013/0197648 A1 | 8/2013 | Boehm et al. | |

\* cited by examiner

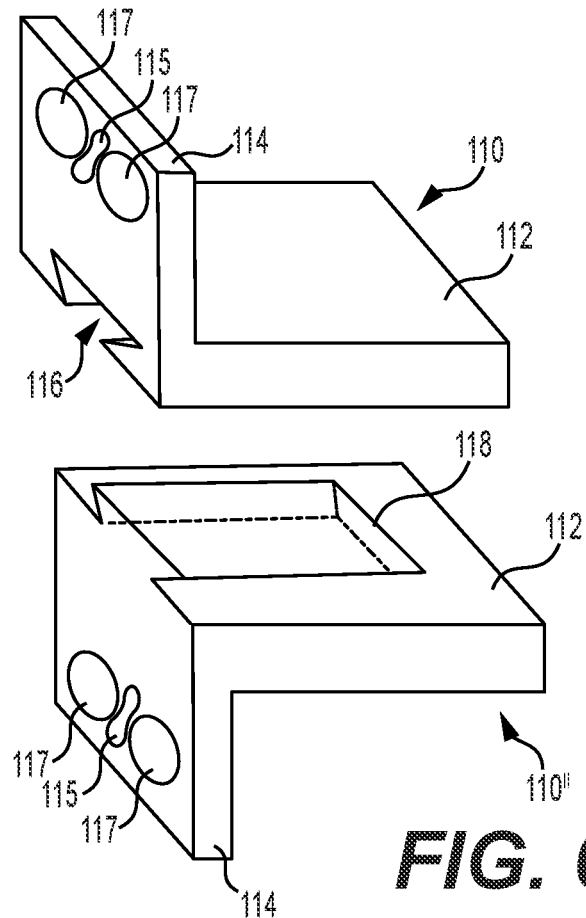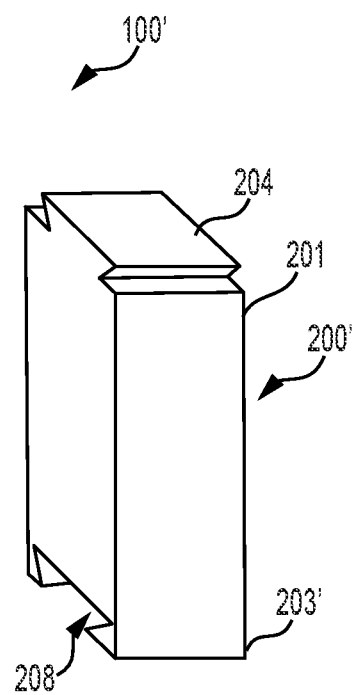
FIG. 6
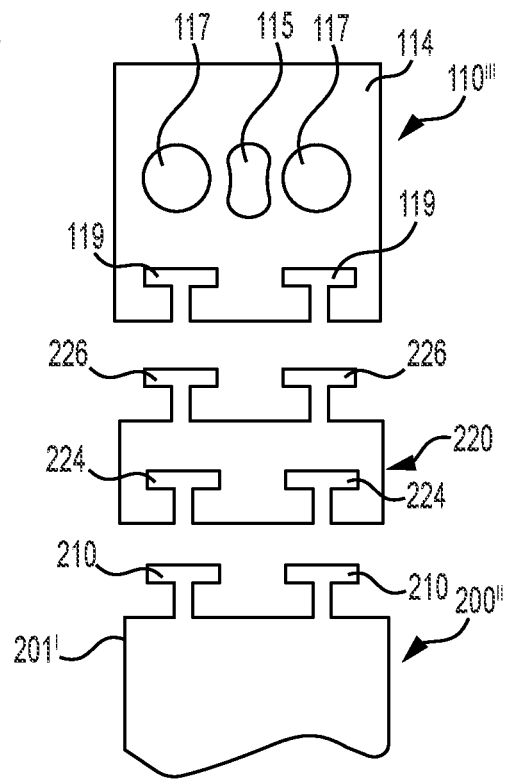
FIG. 7

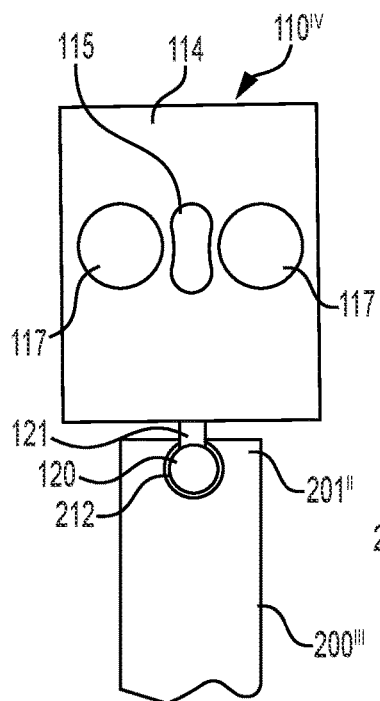 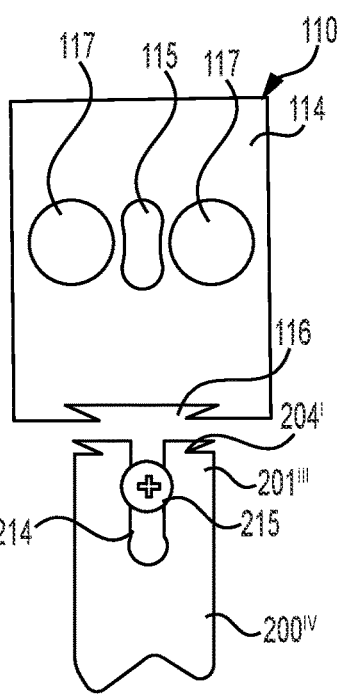 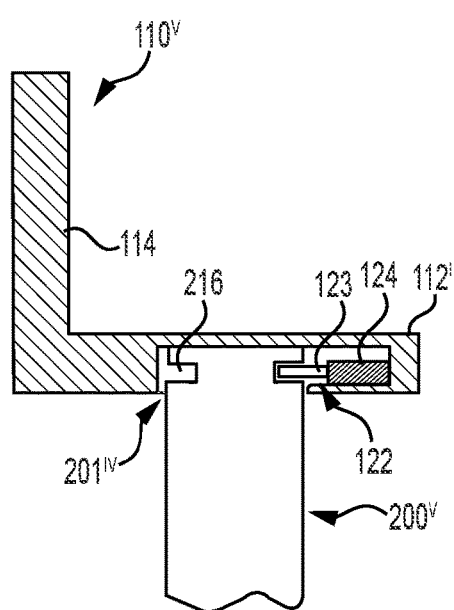
FIG. 8   FIG. 9   FIG. 10
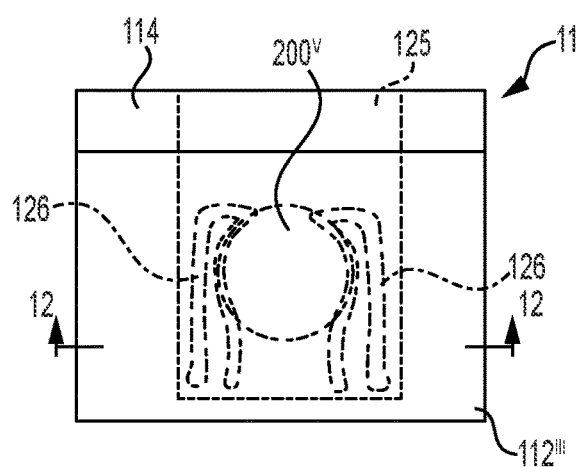 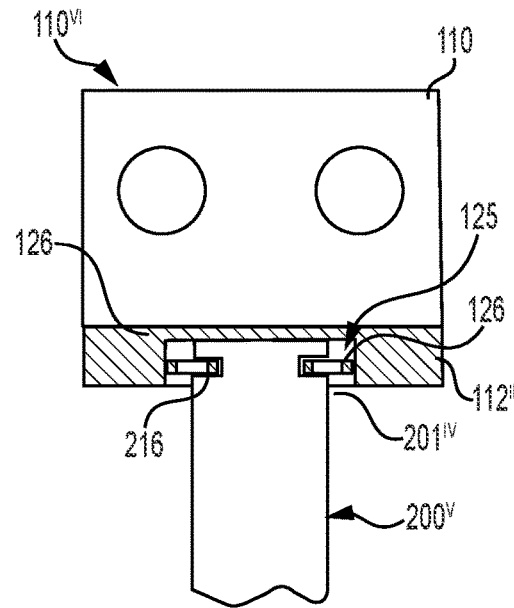
FIG. 11   FIG. 12

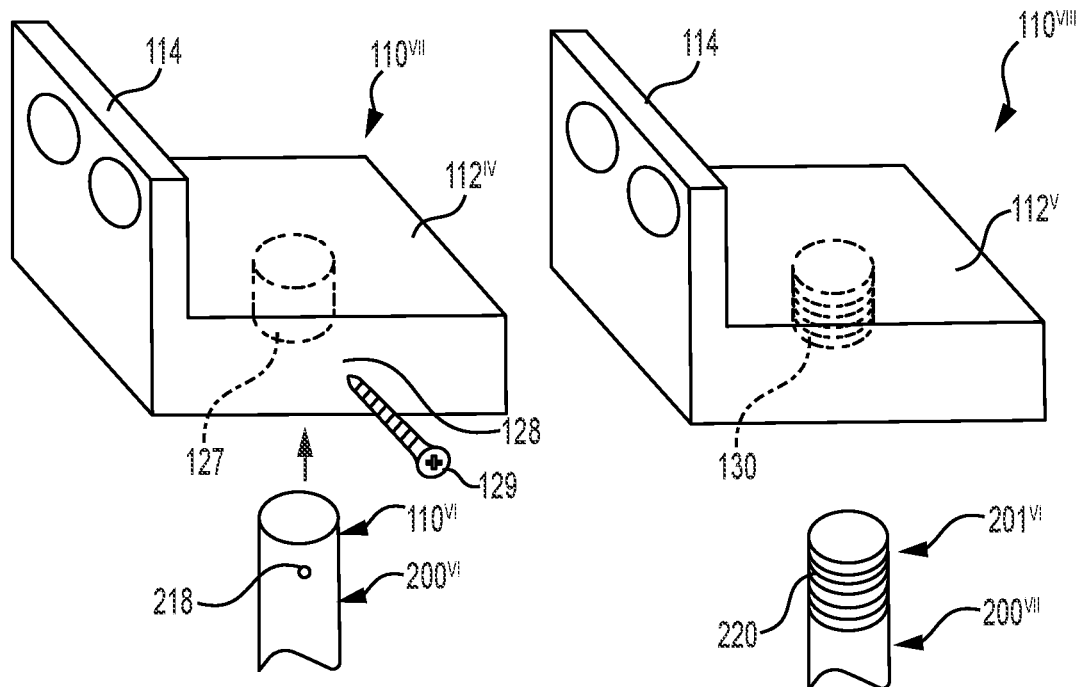
FIG. 13  FIG. 14
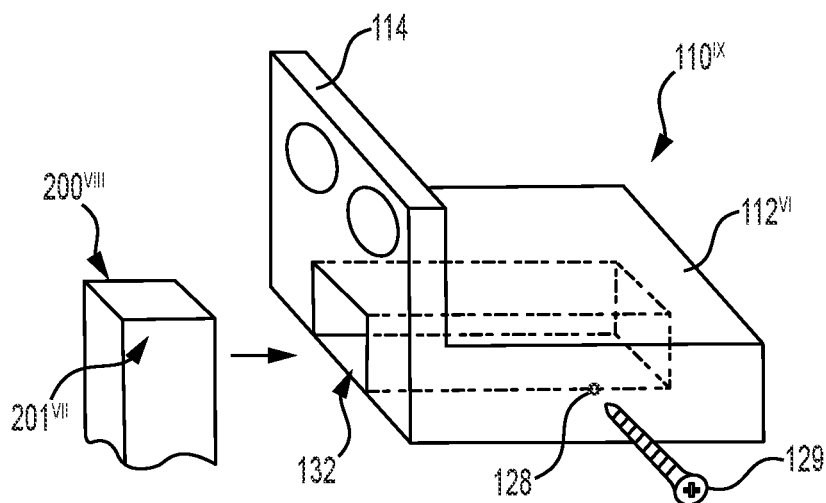
FIG. 15

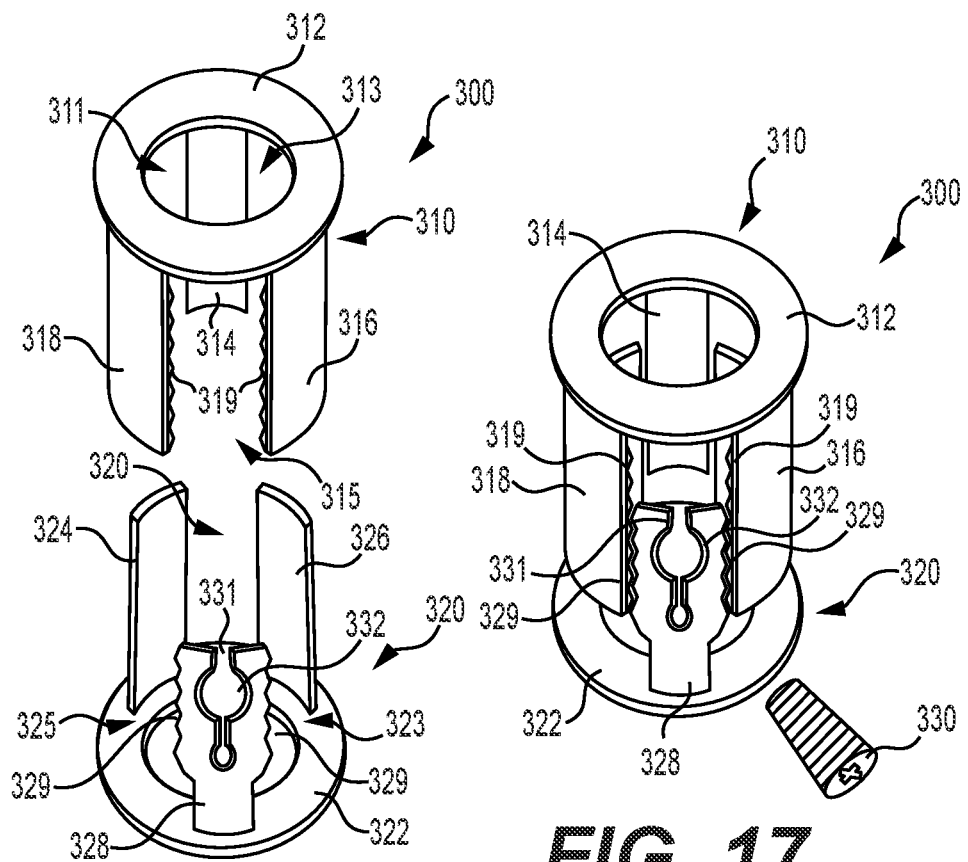
FIG. 16
FIG. 17
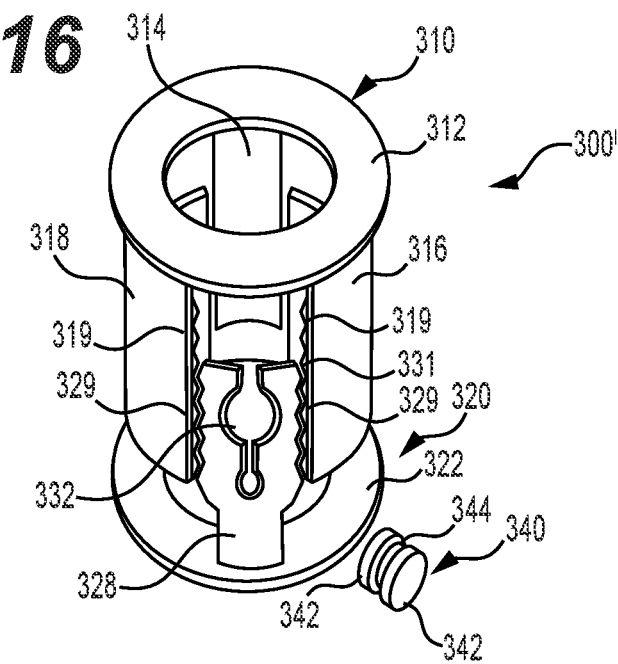
FIG. 18

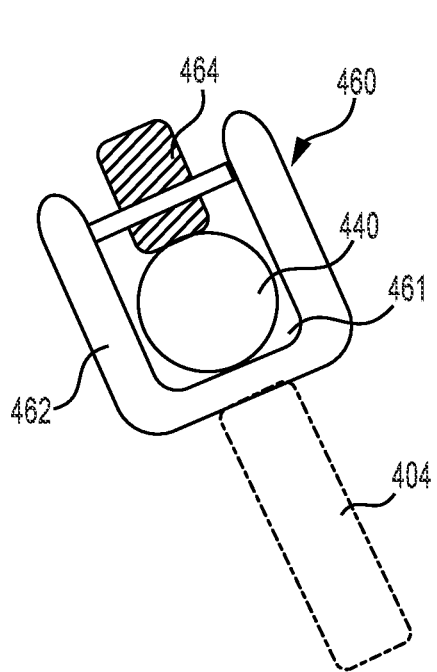
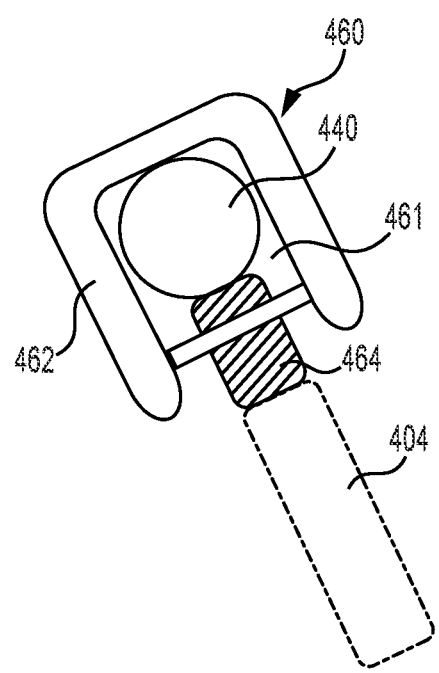
FIG. 39  FIG. 40
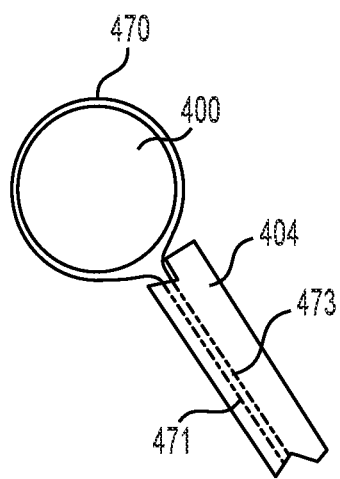
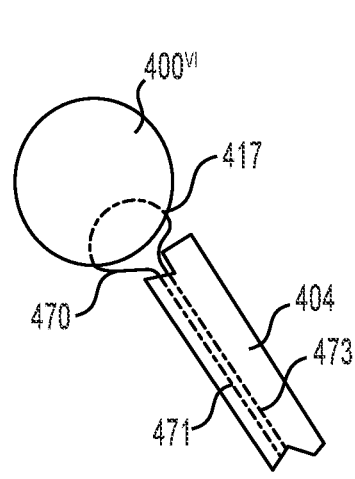
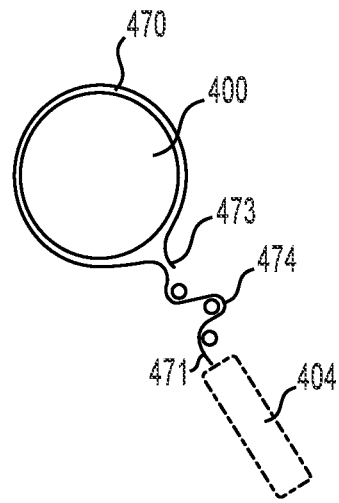
FIG. 41  FIG. 42  FIG. 43

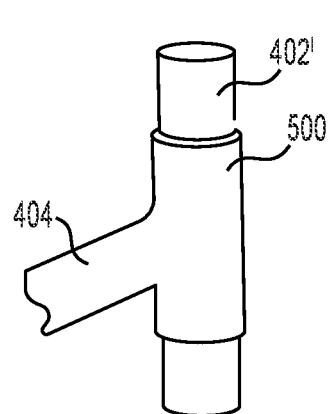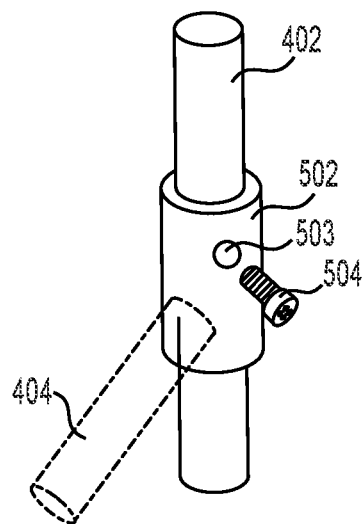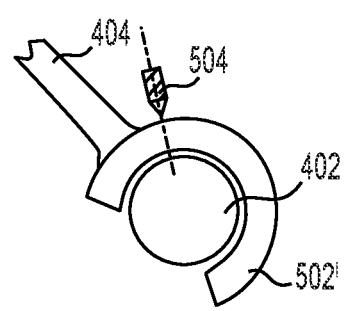
FIG. 52   FIG. 53   FIG. 54
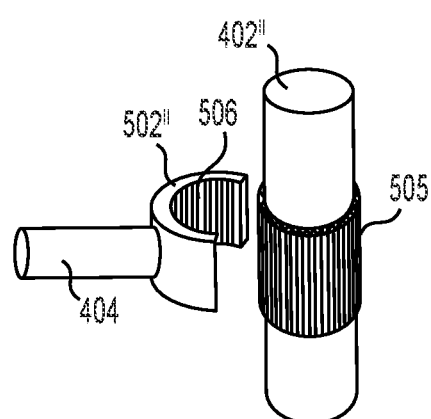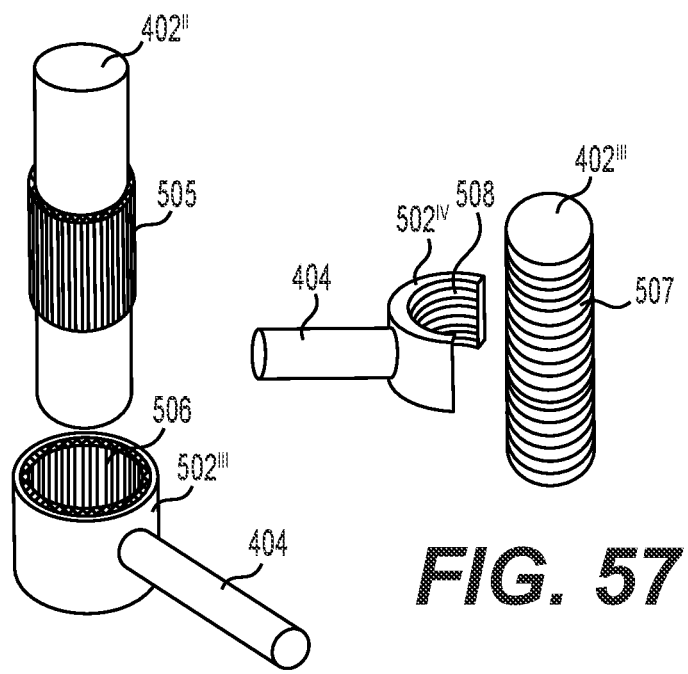
FIG. 55   FIG. 56   FIG. 57

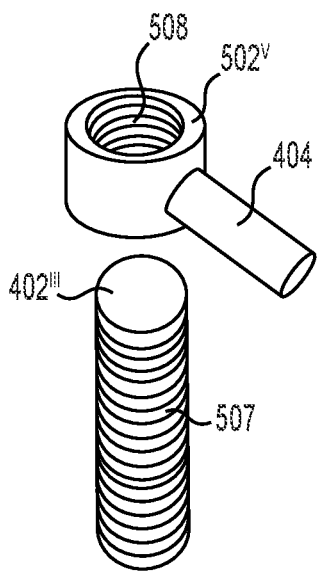
FIG. 58
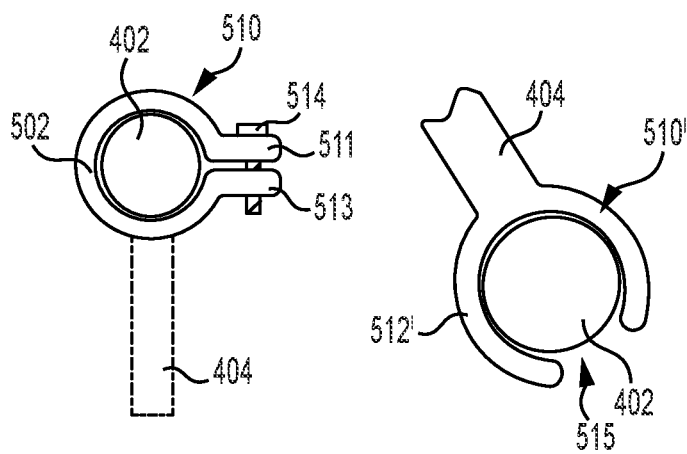
FIG. 59     FIG. 60
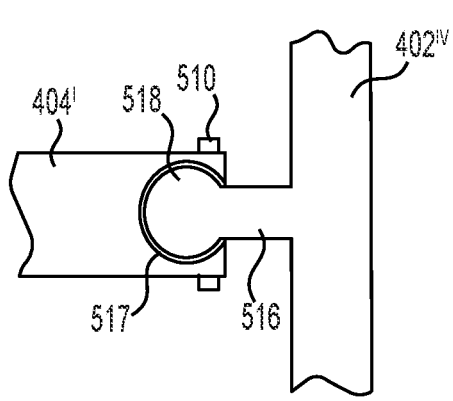
FIG. 61
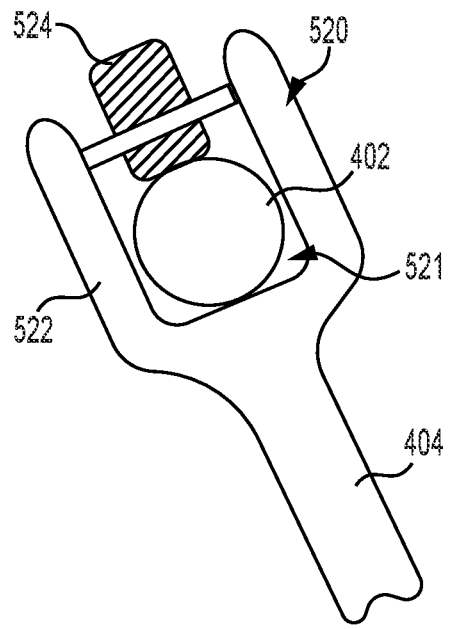
FIG. 62

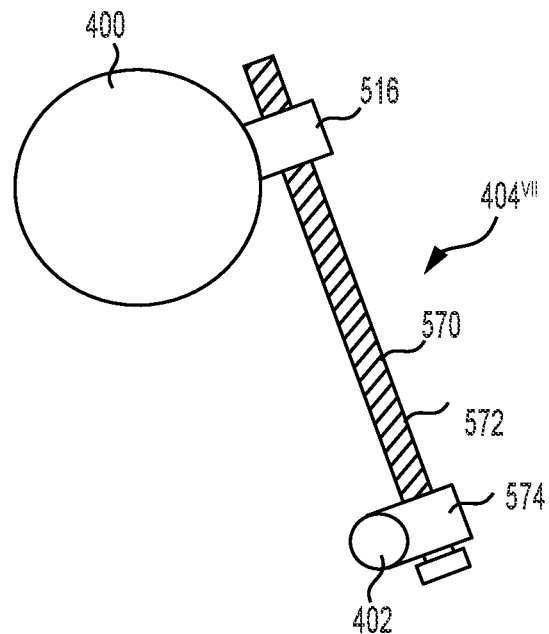
FIG. 70
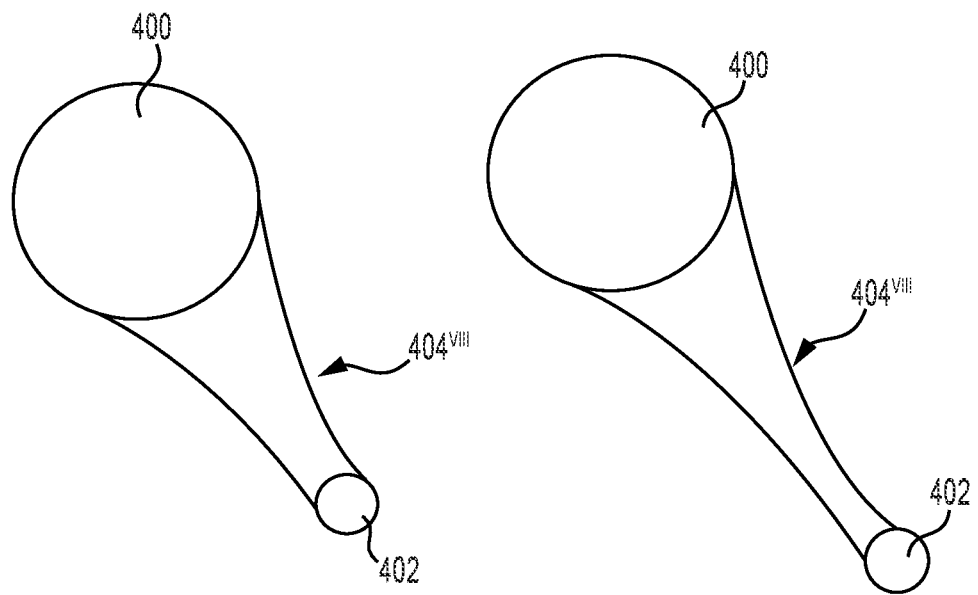
FIG. 71　　　　　FIG. 72

VERTEBRAL IMPLANTS AND ATTACHMENT ASSEMBLIES

CROSS-REFERENCE TO RELATED APPLICATIONS

This application is a continuation of U.S. application Ser. No. 17/070,256, filed on Oct. 14, 2020 (published as U.S. Pat. Pub. No. 2021-0022887), which is a continuation of U.S. application Ser. No. 15/178,814, filed on Jun. 10, 2016, now U.S. Pat. No. 10,842,651, the entire contents of each of which is incorporated by reference in their entireties herein for all purposes.

FIELD OF THE INVENTION

The present disclosure relates to systems and devices for interbody fusion and/or supporting the spine after removal of at least a part of a vertebra. More particularly, the disclosure relates to interbody implants and vertebral body replacement implant assemblies and attachment assemblies.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

Corpectomy surgeries are typically comprised of two parts. The first part includes resection of a portion or all of a one or more vertebral bodies and replacement of resected bone with a VBR (vertebral body replacement) graft. The second part includes stabilizing of the VBR graft using plating on the anterior aspects of the vertebral bodies or, more commonly; posterior screws with rods. The VBR graft may be attached to the posterior rods and/or screws used for stabilization. There are three aspects to achieving this: 1) attaching the stabilizer to the VBR, 2) attaching the stabilizer to the posterior rod, and 3) controlling the length of the stabilizer between the VBR and the posterior rod.

Another solution is to insert an implant or spacer in place of the disc to restore the height and to promote fusion between adjacent vertebral bodies. In some embodiments, additional fixation, in the form of plates or rods, may also be needed to stabilize the spinal segment. The interbody fusion devices may be used following a discectomy procedure to promote fusion between the vertebrae.

In recent years, several artificial materials and implants have been developed, such as, for example, titanium cages, ceramic, ceramic/glass, plastic or PEEK, and carbon fiber spacers. Recently, various expandable prosthetics or expandable cages have been developed and used for vertebral body replacement and/or interbody fusion. The expandable prosthetic devices are generally adjustable to the size of the cavity created by a corpectomy procedure or the disc space and typically are at least partially hollow to accommodate bone cement or bone fragments to facilitate fusion in vivo. Some expandable implants may be adjusted prior to insertion, while others may be adjusted in situ.

Many expandable implant systems are reliant on distraction of the interbody component, however, such a procedure can be complicated and limit the size of the interbody as the distraction instrument interferes with the insertion of the interbody component.

Another disadvantage with many traditional expandable VBR cages and interbody implants is that they have limited internal space for packing bone graft materials which may inhibit their ability to aid fusion. Additionally, traditional mesh VBR cages cannot be expanded and so are difficult to insert from many surgical approaches.

SUMMARY OF THE INVENTION

To meet these and other needs, devices, systems, and methods for providing vertebral body replacement and/or interbody implants are provided. In particular, implant systems and attachment assemblies are provided. Fixing individual plates directly to the vertebral bodies allows for a customized fit to varying vertebral body morphology. Features on the plates that allow distraction or compression allow for the interbody component to be placed into a small/tight space more easily than any system reliant on interbody distraction as the instrument does not interfere with the insertion of the interbody component. If the interbody component can be custom fitted/cut to the exact space between the plates, a custom 'best' fit can be obtained with minimized stress concentrations placed on the vertebral bodies.

Fixing the VBR graft to the posterior rod(s) improves construct stiffness and reduces migration of the VBR. The attachment assemblies described herein provide ease of use, precise control of distance between the VBR graft and posterior rods, attach to differing geometries and posterior rod attachment mechanisms that attach from multiple angles.

In at least one embodiment, a prosthetic implant for engagement between first and second vertebrae is provided. The implant includes a first plate configured for attachment to the first vertebrae and defining a first interbody connection member and a second plate configured for attachment to the second vertebrae and defining a second interbody connection member. An interbody component includes a body with a first end defining a first plate connection member configured for connection to the first interbody connection member and a second end defining a second plate connection member configured for connection to the second interbody connection member. A method of inserting the implant is also provided.

In at least one embodiment, a prosthetic implant for engagement between first and second vertebrae and including first and second interdigitating bodies is provided. The first body includes a first plate with a plurality of spaced apart first legs extending from the first plate. At least two of the first legs define inwardly extending first projections. The second body includes a second plate with a plurality of spaced apart second legs extending from the second plate. At least one of the second legs is an expandable leg and defines second projections along its outward edges. The first and second bodies are interdigitated such that the first legs extend into the spaces defined between the second legs and the second legs extend into the spaces defined between the first legs in an orientation wherein the second projections are aligned with the first projections. A locking mechanism is configured to engage the expandable leg and splay the outward edges outward such that the second projections engage and lock with the first projections.

In at least one embodiment, a prosthetic implant assembly including a vertebral body replacement graft, a posterior rod spaced a distance from the vertebral body replacement graft and an adjustable stabilizer is provided. The adjustable stabilizer is configured such that adjustment of the adjustable stabilizer adjusts the distance between the vertebral body replacement graft and the posterior rod.

Although generally described herein with reference to VBR where a corpectomy has taken place, it will be appreciated that likewise the embodiments may apply equally to an interbody fusion where only a discectomy has occurred and the vertebra or vertebrae remain in place.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 6 is an exploded isometric view of an implant assembly in accordance with another embodiment.

FIG. 7 is an exploded rear elevation view of an interbody component, an expansion component and plate of an implant assembly in accordance with another embodiment.

FIG. 8 is a rear elevation view of an interbody component and plate of an implant assembly in accordance with another embodiment.

FIG. 9 is an exploded rear elevation view of an interbody component and plate of an implant assembly in accordance with another embodiment.

FIG. 10 is a cross-sectional view of an interbody component and plate of an implant assembly in accordance with another embodiment.

FIG. 11 is a top plan view of an interbody component and plate of an implant assembly in accordance with another embodiment.

FIG. 12 is a cross-sectional view along the line 12-12 of FIG. 11.

FIG. 13 is an exploded isometric view of an interbody component and plate of an implant assembly in accordance with another embodiment.

FIG. 14 is an exploded isometric view of an interbody component and plate of an implant assembly in accordance with another embodiment.

FIG. 15 is an exploded isometric view of an interbody component and plate of an implant assembly in accordance with another embodiment.

FIG. 16 is an exploded isometric view of an implant assembly in accordance with another embodiment.

FIG. 17 is an assembled isometric view of the implant assembly of FIG. 16.

FIG. 18 is an isometric view of an implant assembly in accordance with another embodiment.

FIG. 39 is a top plan view of another exemplary embodiment of a VBR graft attachment assembly.

FIG. 40 is a top plan view of another exemplary embodiment of a VBR graft attachment assembly.

FIG. 41 is a top plan view of another exemplary embodiment of a VBR graft attachment assembly.

FIG. 42 is a top plan view of another exemplary embodiment of a VBR graft attachment assembly.

FIG. 43 is a top plan view of another exemplary embodiment of a VBR graft attachment assembly.

FIG. 52 is an isometric view of another exemplary embodiment of a posterior rod attachment assembly.

FIG. 53 is an isometric view of another exemplary embodiment of a posterior rod attachment assembly.

FIG. 54 is a top plan view of another exemplary embodiment of a posterior rod attachment assembly.

FIG. 55 is an exploded isometric view of another exemplary embodiment of a posterior rod attachment assembly.

FIG. 56 is an exploded isometric view of another exemplary embodiment of a posterior rod attachment assembly.

FIG. 57 is an exploded isometric view of another exemplary embodiment of a posterior rod attachment assembly.

FIG. 58 is an exploded isometric view of another exemplary embodiment of a posterior rod attachment assembly.

FIG. 59 is a top plan view of another exemplary embodiment of a posterior rod attachment assembly.

FIG. 60 is a top plan view of another exemplary embodiment of a posterior rod attachment assembly.

FIG. 61 is a side elevation view of another exemplary embodiment of a posterior rod attachment assembly.

FIG. 62 is a top plan view of another exemplary embodiment of a posterior rod attachment assembly.

FIG. 70 is a top plan view of another exemplary embodiment of an adjustable stabilizer.

FIG. 71 is a top plan view of another exemplary embodiment of an adjustable stabilizer in a first condition.

FIG. 72 is a top plan view of the adjustable stabilizer of FIG. 71 in a stretched condition.

DETAILED DESCRIPTION OF THE INVENTION

Figure 1:
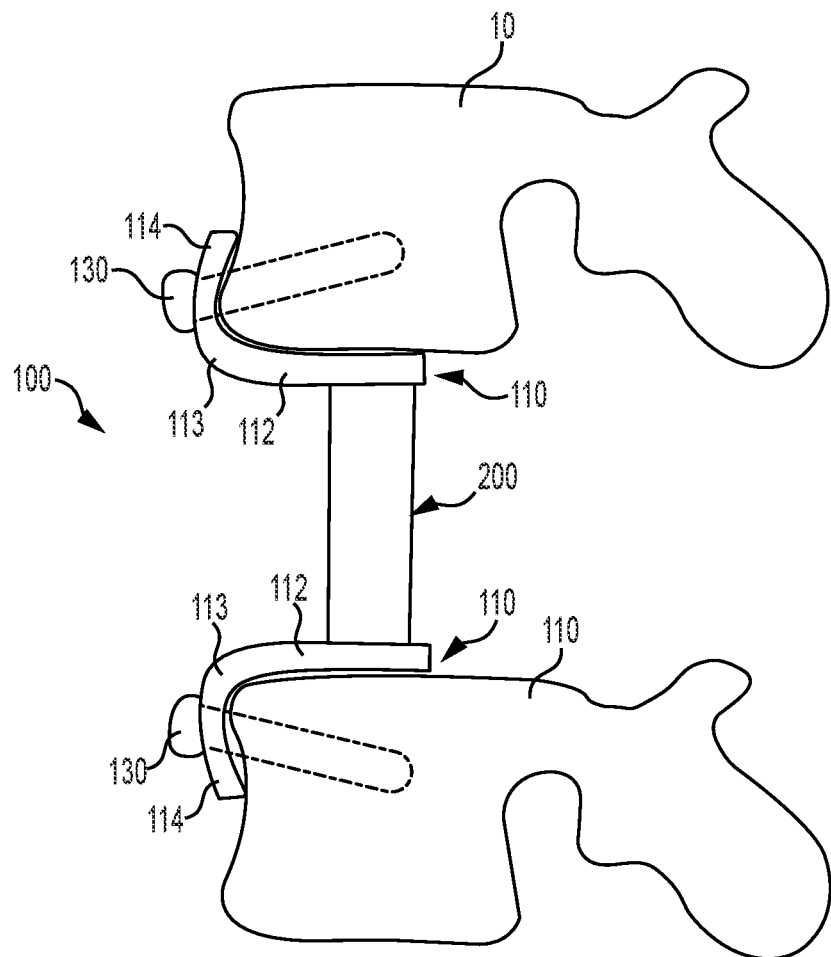
FIG. 1 is a side elevation view of an implant assembly according to an exemplary embodiment attached between vertebrae.

In the drawings, like numerals indicate like elements throughout. Certain terminology is used herein for convenience only and is not to be taken as a limitation on the present invention. The following describes preferred embodiments of the present invention. However, it should be understood, based on this disclosure, that the invention is not limited by the preferred embodiments described herein.

Referring to FIGS. 1 and 3-5, an exemplary embodiment of an implant assembly 100 will be described. The implant assembly 100 is illustrated positioned between a pair of vertebrae 10. The implant assembly 100 generally includes a pair of plates 110 with an interbody component 200 secured between the plates 110. In the present embodiment, each plate 110 has a generally L-shaped configuration with a lateral portion 112 connected to a vertical portion 114 via a bend portion 113. As illustrated in FIG. 1, the bend portion 113 and the lateral and vertical portions 112, 114 may have a configuration which complements the configuration of the vertebrae 10 or other structure to which the plate 110 is connected. The plates 110 are not limited to such and may have other configurations, for example, a right angle between the lateral portion 112 and vertical portion 114 such that the plate 110 may have more universal use. As another alternative, one or both of the plates 110' may include only the lateral portion 112' such that the plate 110' only extends along the facing surface of the vertebrae, as illustrated in FIG. 2.

Figure 2:
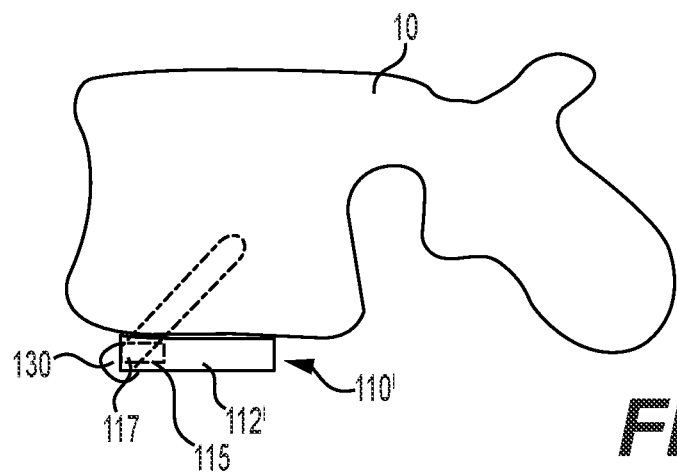
FIG. 2 is a side elevation view of an alternative plate of the implant assembly attached to a vertebra.
Figure 4:
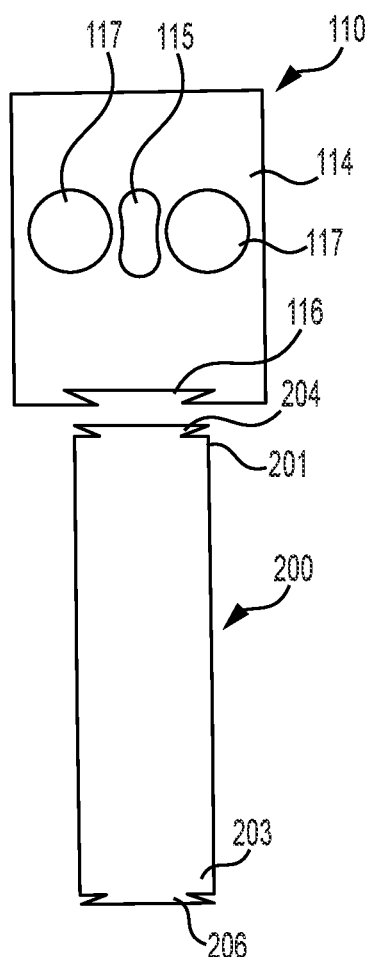
FIG. 4 is an exploded rear elevation view of an exemplary interbody component and plate of the implant assembly of FIG. 1.

With reference to FIGS. 1, 2 and 4, in the illustrated embodiments, each of the plates 110, 110' includes one or more screw holes 117 which facilitate connection of the plate 110 to a respective vertebra via screws 130. While screws are illustrated, other fasteners may alternatively or additionally be utilized to connect the plates 110, 110' to the vertebrae, for example, pins, staples or spike locking/blocking mechanisms. The plates 110, 110' are secured to the vertebral body 10 at the level(s) above and/or below the operative level(s).

Figure 3:
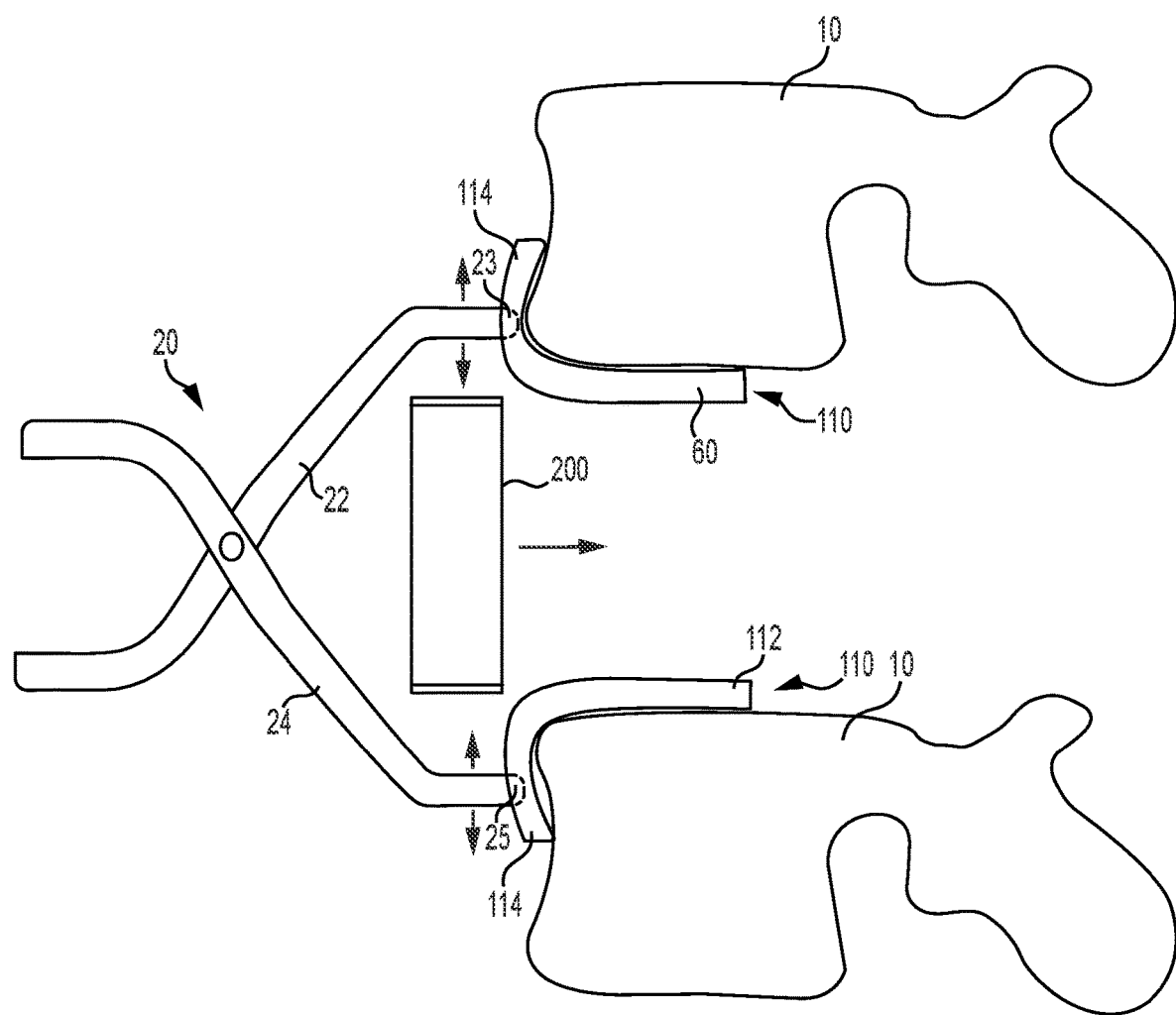
FIG. 3 is a side elevation view illustrating an exemplary implantation of the implant assembly of FIG. 1 utilizing a distraction/compression instrument.

Each of the plates 110, 110' also preferably includes an instrument receiving opening 115. With reference to FIG. 3, an exemplary implant instrument 20 includes a pair of crossing branches 22, 24, with each branch 22, 24 including a respective tip 23, 25 configured to be received in an instrument receiving opening 115. With the plates 110 secured to the vertebrae 10 and the tips 23, 25 received in the respective instrument receiving openings 115, the instrument 20 can easily facilitate distraction or compression of the vertebrae 10. While instrument receiving openings are illustrated, the plates 110, 110' may be provided with other features which facilitate engagement by the implant instrument 20.

Fixing the individual plates 110 directly to the vertebral bodies allows for a customized fit to varying vertebral body morphology. Distraction or compression via the plates 110, 110' allows for the interbody component 200 to be placed into a small/tight space more easily than systems which are reliant on interbody distraction as the instrument does not interfere with the insertion of the interbody component. Positioning a custom fit/cut interbody component 200 into the exact space between the distracted/compressed plates, a custom 'best' fit can be obtained with minimized stress concentrations placed on the vertebral bodies.

While the interbody component 200 is illustrated as a solid tubular member, it is understood that the interbody component 200 is not limited to such. The interbody component 200 can have central hole(s) to allow bone graft materials be placed. It can also have hole(s) through its external walls that allow placement of grafting material. The interbody component 200 can be fixed in height or can be an expanding body, for example, as described in U.S. Pat. No. 8,591,585.

Figure 5:
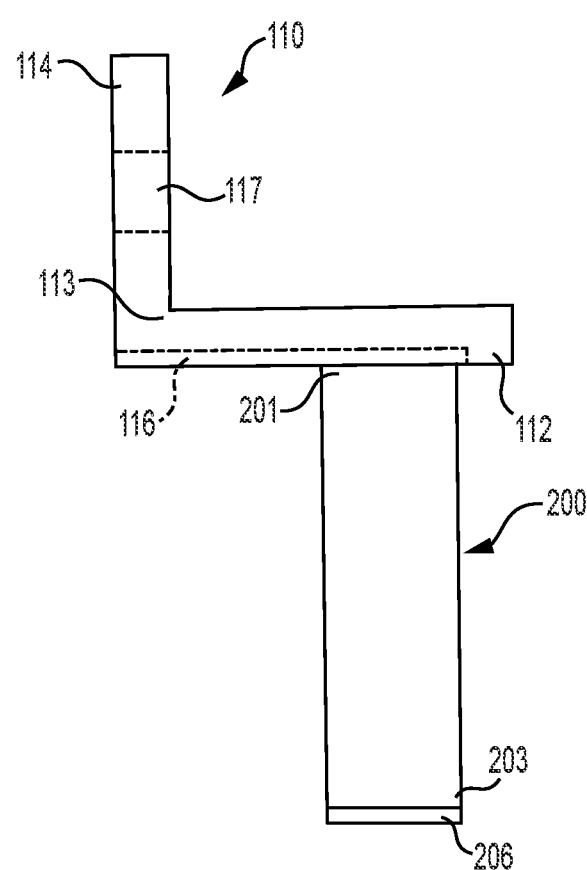
FIG. 5 is a side elevation view illustrating the interbody component and plate of FIG. 4 in an assembled condition.

Referring to FIGS. 4 and 5, to facilitate connection of the interbody component 200 to the plates 110, the interbody component 200 includes connection members at each end 201, 203 thereof which complement connection members of the plates 110. In the illustrated embodiment, each end 201, 203 of the interbody component 200 includes a dovetail shaped projection 204, 206 which slidingly engages a corresponding dovetail shaped slot 116 in the plate 110.

Referring to FIG. 6, the plates 110, 110" within the implant assembly 100' may have different configurations, with the interbody member 200' having different end configurations to mate with the different plate configurations. In the illustrated embodiment, the plate 110 is as described above with a dovetail shaped recess 116 configured to receive the dovetail shaped projection 204 on the interbody component 200'. The other plate 110" includes a dovetail shaped projection 118 instead of a slot. The dovetail shaped projection 118 is configured to be received in a dovetail shaped slot 208 on the end 203' of the interbody component 200'. The dovetail shaped projection 118 is also preferably configured to be received into the dovetail shaped slot 116 on the opposite plate 110 such that the plates 110, 110" may be directly connected, omitting the interbody component.

It is further understood that the complimentary connecting elements do not have to have a dovetail shape. For example, the embodiment illustrated in FIG. 7 shows the plate 110''' having a pair of T-shaped slots 119 and the interbody component 200" having complementary T-shaped projections 210 at the end 201'. Additionally, an extension component 220 is configured to be positioned between the interbody component 200" and the plate 110''' to customize the length of the interbody component between the plates. The extension component 220 has complementary connecting elements, namely, T-shaped slots 224 and T-shaped projections 226.

As another exemplary alternative, FIG. 8 illustrates an embodiment wherein the plate 110' includes an extension 121 with a spherical head 120. The spherical head 120 is configured to be received in a slot 212 having a circular cross-section in the end 201''' of the interbody component 200'''. Engagement of the spherical head 120 in the circular slot 212 allows omnidirectional adjustment between the plate $110^{iv}$ and the interbody component 200'''.

With reference to FIGS. 9-15, exemplary connecting configurations with additional locking mechanisms will be described. In the embodiment illustrated in FIG. 9, the plate 110 has a dovetail slot 110 while the end 201''' has dovetail shaped projection 204' which is expandable after it is positioned within the slot 110. To facilitate expansion, a notch 214 extends through the interbody component $200^{iv}$. To lock the interbody component $200^{iv}$ relative to the plate 110, a tapered screw 215 is threaded into the notch 214 such that the dovetail shaped projection 204' expands as the screw 215 is advanced.

In the embodiment illustrated in FIG. 10, the interbody component $200^{v}$ includes an annular groove 216 in the end $201^{iv}$. A locking pin 123 is positioned within a chamber 122 in the lateral portion 112" of the plate $110^{v}$. A spring 124 biases the pin 123 into engagement with the annular groove 216 to lock the interbody component $200^{v}$ relative to the plate $110^{v}$.

In the embodiment illustrated in FIGS. 11 and 12, the interbody component $200^{v}$ again includes an annular groove 216 in the end $201^{iv}$. A slot 125 in the lateral portion 112''' of the plate $110^{vi}$ is configured to receive opposed leaf springs 126 which extend into the annular groove 216 to lock the interbody component $200^{v}$ relative to the plate $110^{vi}$.

In the embodiment illustrated in FIG. 13, the lateral portion $112^{iv}$ of the plate $110^{vii}$ includes a bore 127 in the lower surface thereof. The interbody component $200^{vi}$ has a complementary shape to the bore 127 and includes a screw receiving hole 218 in the end $201^{v}$. A screw 129 extends through a hole 128 in the lateral portion $112^{iv}$ of the plate $110^{vii}$ and into the screw receiving hole 218 to lock the interbody component $200^{vi}$ relative to the plate $110^{vii}$.

In the embodiment illustrated in FIG. 14, the lateral portion $112^{v}$ of the plate $110^{vii}$ includes a threaded bore 130 in the lower surface thereof. The interbody component $200^{vii}$ has a complementary shape to the bore 127 and includes threads 220 at the end $201^{vi}$. The threads 220 are threadably secured into the threaded bore 130 to lock the interbody component $200^{vii}$ relative to the plate $110^{viii}$.

In the embodiment illustrated in FIG. 15, the lateral portion $112^{vi}$ of the plate $110^{ix}$ includes a slot 132 configured to receive the end $201^{vii}$ of the interbody component $200^{viii}$. A screw 129 extends through a hole 128 in the lateral portion $112^{vi}$ of the plate $110^{ix}$ and into engagement with the interbody component $200^{viii}$ to lock the interbody component $200^{viii}$ relative to the plate $110^{ix}$.

Fixing of the plate to the interbody component is not limited to the described embodiments. Other methods of connection may also be utilized, for example, setscrews, pins, staples, rivets, adhesives, and other spring connections.

Referring to FIGS. 16 and 17, an implant assembly 300 in accordance with another embodiment will be described. The implant assembly 300 includes a pair of cage bodies 310 and 320 which interdigitate and can be separated and locked in position relative to one another. The first cage body 310 includes a plate 312 with a plurality of legs 314, 316 and 318 extending therefrom. The legs 314, 316, 318 are radially spaced from one another to define respective spaces 311, 313, 315. At least two of the legs 316, 318 define a series of inwardly extending projections 319.

The second cage body 320 includes a plate 322 with a plurality of legs 324, 326 and 328 depending therefrom. The legs 324, 326, 328 are radially spaced from one another to define respective spaces 321, 323, 325. The leg 328 has projections 329 extending along each edge. A slot 331 extends into the leg 328 between the projections 329 with a screw receiving opening 332 along the slot 331.

The interdigitating bodies 310 and 320 slide together with the legs 314, 316, 318 received in the spaces 321, 323, 325 of the body 320 and the legs 324, 326, 328 received in the spaces 311, 313, 315. The bodies 310 and 320 are oriented relative to one another such that the projections 329 are aligned with the projections 319. The bodies 310 and 320 can be separated from one another by a distractor-type instrument, for example, the instrument 20 illustrated in FIG. 3. Once the bodies 310 and 320 have been separated, a tapered screw 330 is advanced into the screw receiving opening 332 in the leg 328. As the screw 330 is advance, the sides of the leg 328 splay outwardly with the projections 329 engaging the projections 319. Expansion allows the implant assembly 300 to fit into a smaller/shorter interbody space and distraction requirements are reduced or eliminated. Additionally, graft packing capacity is maximized when compared to a telescoping expandable design.

FIG. 18 illustrates an alternative embodiment of the implant assembly 300'. The implant assembly 300' is the same as in the previous embodiment except that the screw is replaced by a cam mechanism 340. The cam mechanism 340 include opposed larger ends 342 and an intermediate camming portion 344. The camming portion 344 has a double-D configuration such that the camming portion 344 has a height which is greater than the width. The cam mechanism 340 is positioned in the opening 332 with the ends 342 maintaining the cam mechanism 340 in position. To lock the bodies 310, 320 relative to one another, the cam mechanism 340 is rotated until the height of the camming portion 344 extends generally parallel to the plate 322 such that the camming portion 344 causes the sides of the leg 328 to splay outwardly with the projections 329 engaging the projections 319.

Figures 19, 20:
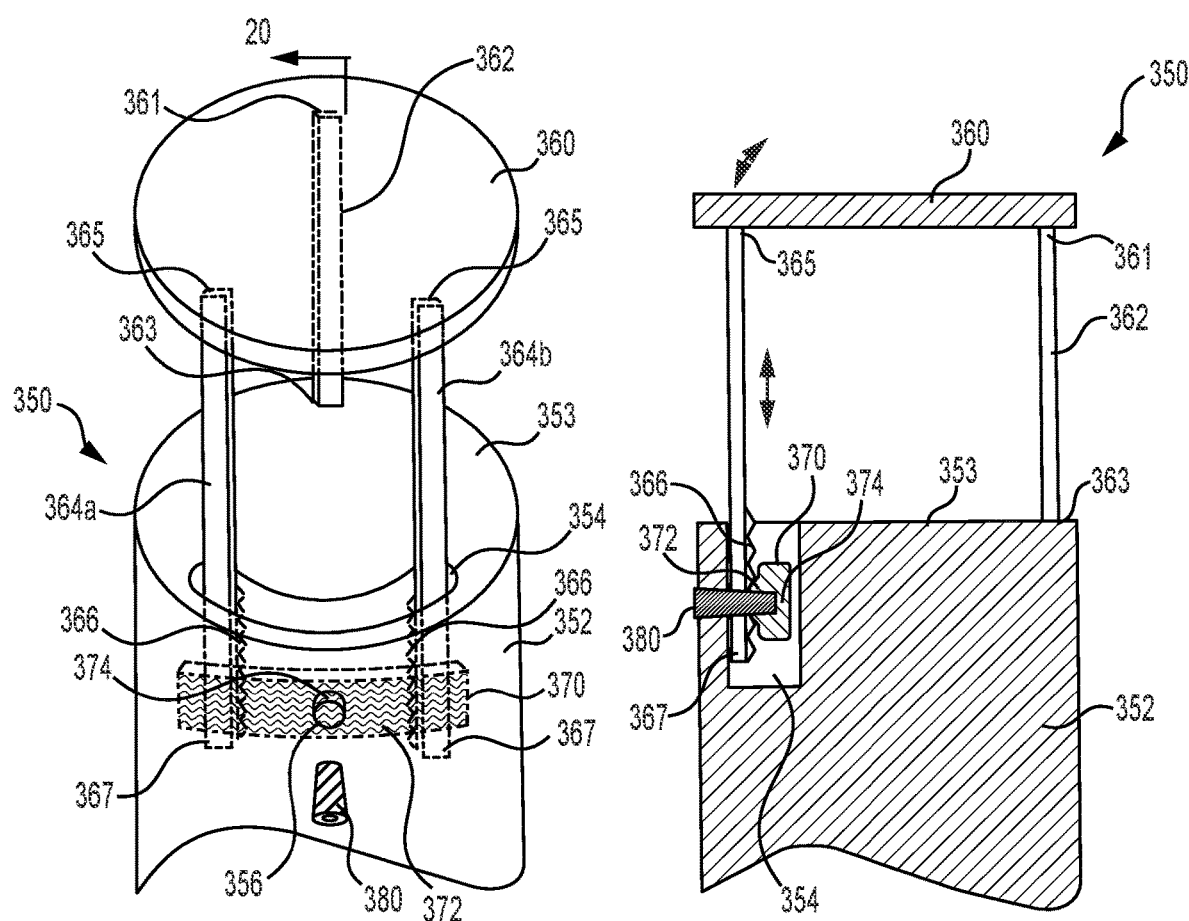
FIG. 19 is an isometric view of an implant assembly in accordance with another embodiment.
FIG. 20 is a cross-sectional view along the line 20-20 in FIG. 19.

Referring to FIGS. 19 and 20, an alternative embodiment a body 350 will be described. The body 350 can be used as one of the interbody components 200 described above, as one of the bodies 310, 320 as described above, or in other interbody structures. The body 350 includes a main body 352 and an adjustable end plate 360 at one or both ends. The end plate 360 is supported relative to the main body 352 by a plurality of supports 362, 364a, 364b. In the illustrated embodiment, the supports include a fixed support 362 and a pair of vertically adjustable supports 364a and 364b. The fixed support 362 has a first end 361 fixed to the plate 360 and a second end 363 fixed to an end surface 353 of the main body 352.

Each of the adjustable supports 364a, 364b includes a first end 365 fixed to the plate 360 and an adjustment end 367 which extends into a slot 354 in the main body 352. Each adjustment end 367 includes a plurality of grooves 366 configured to engage grooves 372 on a locking member 370 within the main body 352. A locking screw 380 extends through a hole 356 in the main body 352 and into a threaded bore 374 in the locking member 370. Each of the adjustable supports 364a, 364b is independently linearly adjustable to adjust the angle of the plate 360 relative to the end surface 353. Once a desired orientation is achieved, the locking screw 380 is advanced such that the grooves 372 of the locking member 370 are pulled into engagement with the grooves 366 of the adjustable supports 364a, 364b to lock the adjustable supports 364a, 364b, and thereby the angle of the plate 360, in position. Adjustability of the plate 360 allows the body 350 to fit with patient anatomy with reduced stress concentrations.

Figure 21:
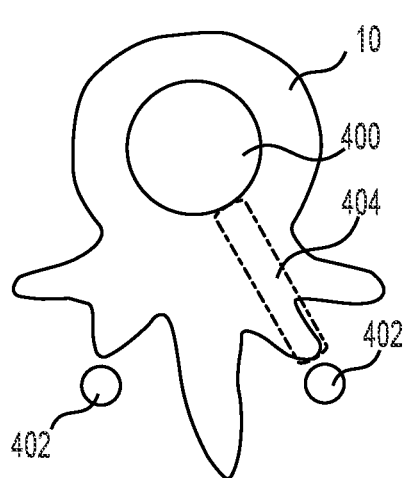
FIG. 21 is a schematic plan view of a vertebral body replacement (VBR) graft, stabilizer and posterior rods positioned relative to a vertebra.

In addition to replacement of resected bone with a VBR (vertebral body replacement) graft, corpectomy surgeries typically also include stabilization using plating on the anterior aspects of the vertebral bodies 10 or, more commonly; posterior screws with rods. Referring to FIGS. 21-72, various components and methods utilized to fix the VBR graft 400 to the posterior rods 402 via stabilizers 404 will be described. The embodiments illustrated in FIGS. 22-50 illustrate components and methods for attaching the stabilizer 404 to the VBR graft 400; FIGS. 51-63 illustrate components and methods for attaching the stabilizer 404 to the posterior rod 402; and FIGS. 64-72 illustrate components and methods for controlling the length of the stabilizer 404 between the VBR graft 400 and the posterior rod 402.

Figure 22:
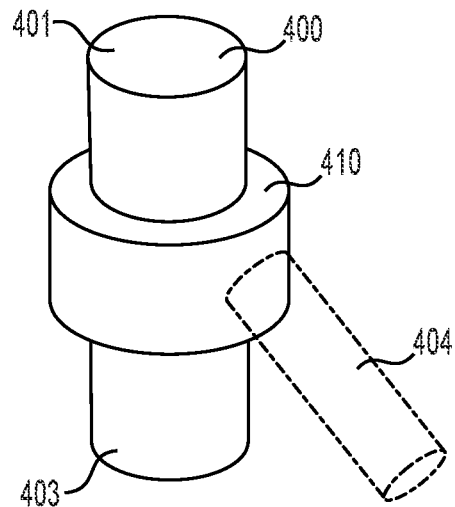
FIG. 22 is an isometric view of an exemplary embodiment of a VBR graft attachment assembly.
Figure 23:
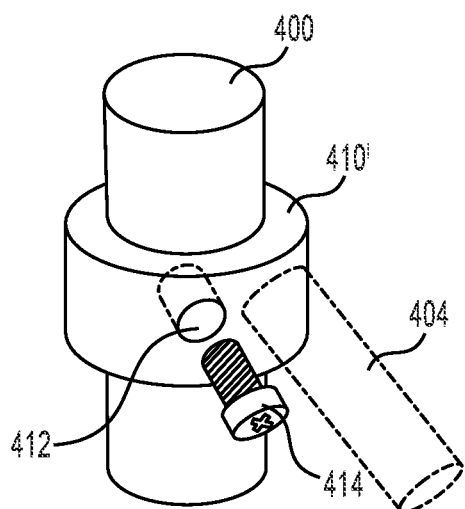
FIG. 23 is an isometric view of another exemplary embodiment of a VBR graft attachment assembly.

Referring to FIGS. 22-29, the VBR graft 400 includes a collar for attachment of the stabilizer. In each of these embodiments, the collar may be formed integrally with the VBR or may be manufactured separately and connected relative thereto. In the embodiment of FIG. 22, the collar 410 is fixedly connected between the ends 401, 403 of the VBR and has a diameter larger than that of the VBR graft 400 such that the collar 410 extends radially outwardly therefrom. The stabilizer 404 is configured to connect to the radially extending collar. Referring to FIG. 23, the fixed collar 410' is substantially the same as the previous embodiment but further includes additional fixation for the stabilizer 404, for example, a bore 412 with an associated screw.

Figure 24:
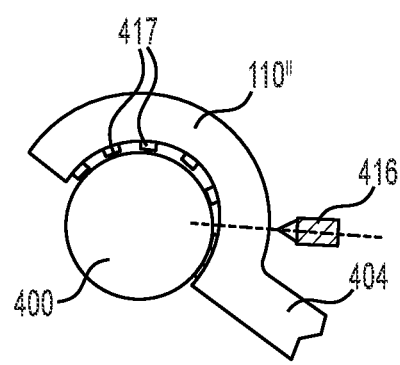
FIG. 24 is a top plan view of an exemplary embodiment of a VBR graft attachment assembly.

Referring to FIG. 24, the collar 410" extends partially about the VBR graft 400. The orientation of the collar 410" and the stabilizer 404 may be set and thereafter fixed relative to the VBR graft 400 via a set screw 416 or the like. Splines 417 or the like may be provided on the inside surface of the collar 410".

Figure 25:
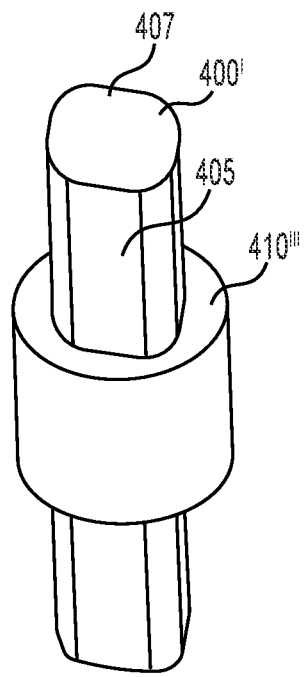
FIG. 25 is an isometric view of another exemplary embodiment of a VBR graft attachment assembly.
Figure 26:
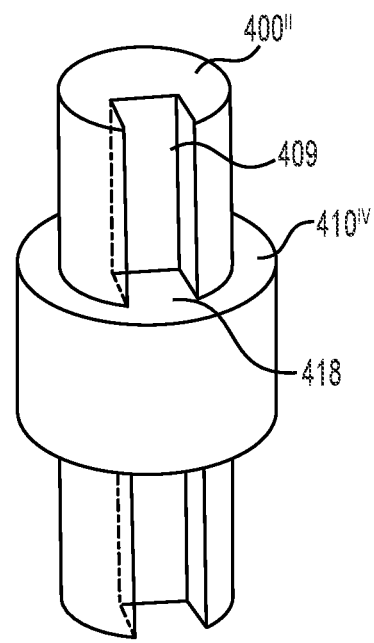
FIG. 26 is an isometric view of another exemplary embodiment of a VBR graft attachment assembly.
Figure 27:
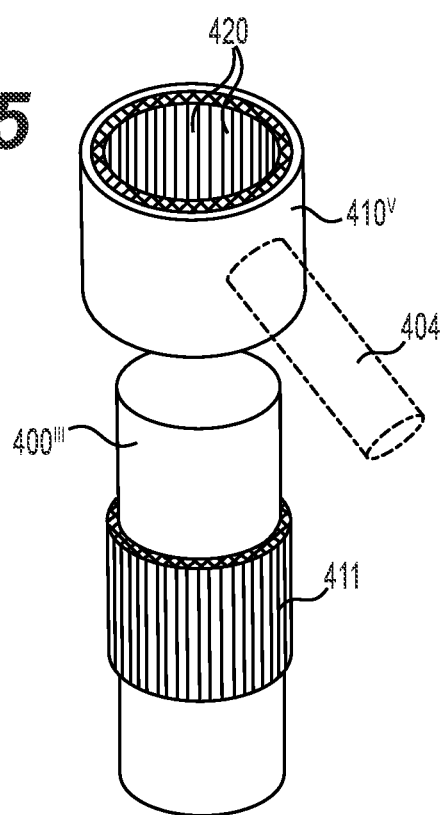
FIG. 27 is an exploded isometric view of another exemplary embodiment of a VBR graft attachment assembly.

Referring to FIGS. 25-27, the collar is configured to mate with the outside geometry of the VBR. In the embodiment illustrated in FIG. 25, the VBR graft 400' is formed with flat sides 405, 407 and the collar 410''' is formed with a complementary configuration. In the embodiment illustrated in FIG. 26, the VBR graft 400'' is formed with an inward channel 409 and the collar 410$^{iv}$ is formed with a complementary projection 418. In the embodiment illustrated in FIG. 27, the VBR graft 400'' is formed with outward splines 411 and the collar 410$^{v}$ is formed with complementary inward splines 420.

Figure 28:
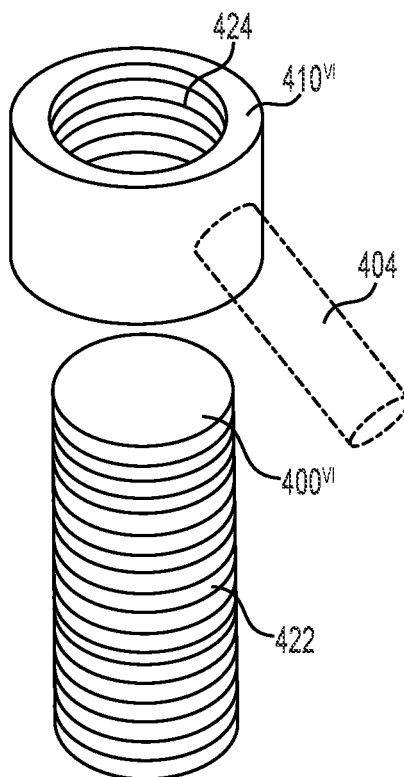
FIG. 28 is an exploded isometric view of another exemplary embodiment of a VBR graft attachment assembly.
Figure 29:
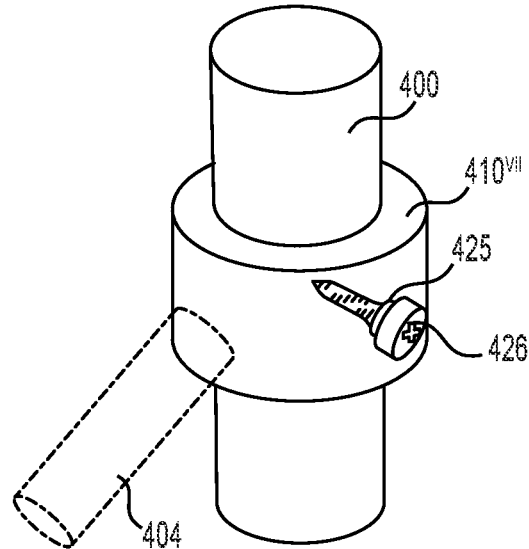
FIG. 29 is an isometric view of another exemplary embodiment of a VBR graft attachment assembly.

Referring to FIGS. 28-29, the collar is adjustable relative to the VBR. In the embodiment illustrated in FIG. 28, at least a portion of the VBR graft 400$^{iv}$ includes external threads 422 and the collar 410$^{vi}$ includes complementary internal threads 424. The collar 410$^{vi}$ may be threadably connected to a desired position along the VBR graft 400$^{vi}$. In the embodiment illustrated in FIG. 29, the collar 410$^{vii}$ includes a through hole 425 through which a set screw 426 extends. Once the collar 410$^{vii}$ is positioned as desired, the set screw 426 is advanced into position against the VBR graft 400 to lock the position.

Figure 30:
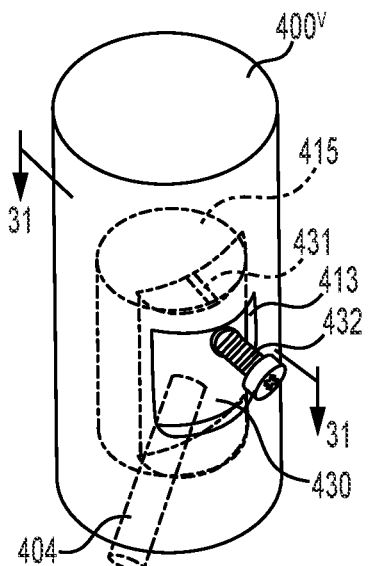
FIG. 30 is an isometric view of another exemplary embodiment of a VBR graft attachment assembly.
Figure 31:
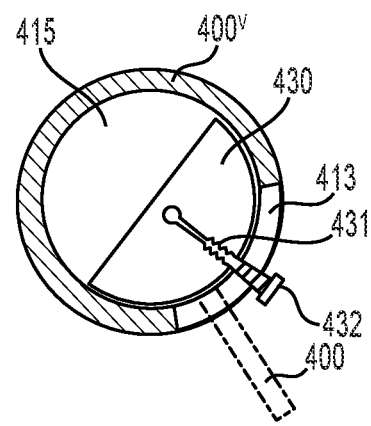
FIG. 31 is a cross-sectional view along the line 31-31 in FIG. 30.

Referring to FIGS. 30-31, the VBR graft 400$^{v}$ includes an opening 413 into an internal chamber 415 in which is positioned an adjustable support block 430. The support block 430 includes a split 431 therein configured to receive a locking screw 432. Once the angular orientation of the support block 430 is as desired, the locking screw 432 is advanced, causing the block 430 to splay into contact with the inside surface of the chamber 415. Alternatively, a screw may extend through the VBR graft 400$^{v}$ into engagement with the support block 430 to lock the position of the support block 430.

Figure 32:
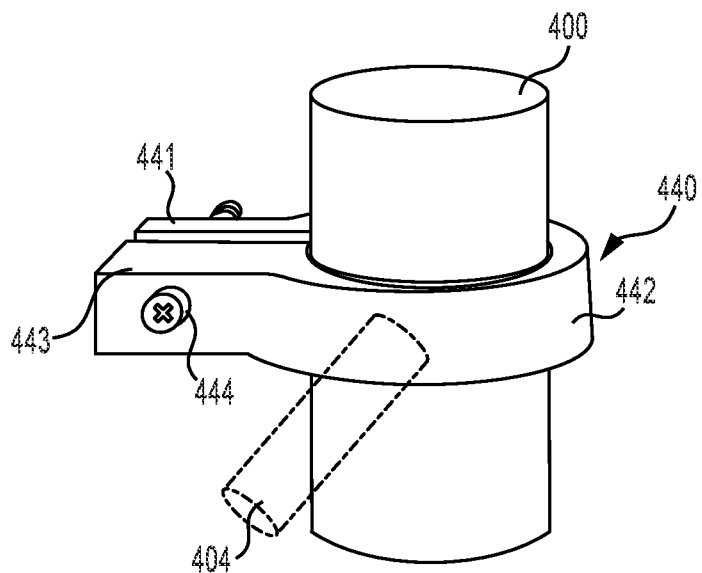
FIG. 32 is an isometric view of another exemplary embodiment of a VBR graft attachment assembly.
Figure 33:
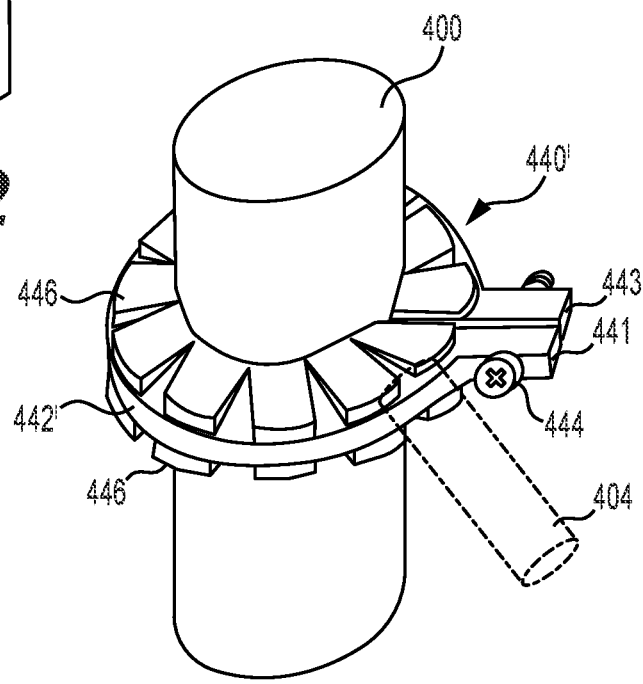
FIG. 33 is an isometric view of another exemplary embodiment of a VBR graft attachment assembly.
Figure 34:
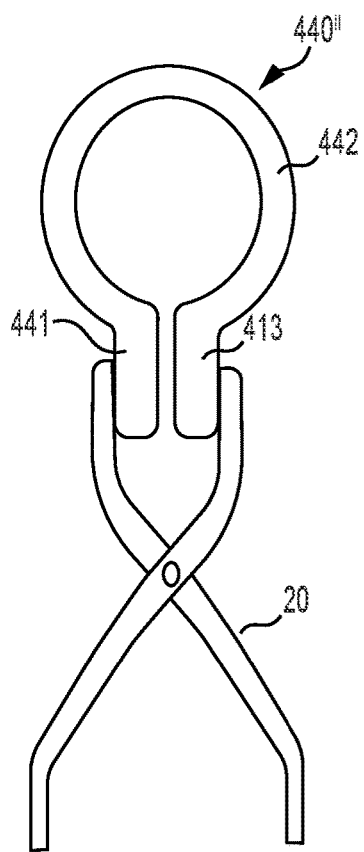
FIG. 34 is a top plan view of another exemplary embodiment of a VBR graft attachment assembly compressed using a distraction/compression instrument.

Referring to FIGS. 32-38, the VBR graft 400 includes a clamp for attachment of the stabilizer. In the embodiment of FIG. 32, the clamp 440 includes a collar portion 442 which extends about the VBR graft 400 to a pair of opposed legs 441, 443. A screw 444 extends through the legs 443, 444. Advancing of the screw 444 brings the legs 441, 443 together, tightening the collar portion 442 about the VBR graft. The stabilizer 404 is configured for attachment to the clamp 440. Referring to FIG. 33, the clamp 440' is substantially the same as the previous embodiment except for the collar portion 442' which includes a plurality of ridges 446 or other shapes which complement the stabilizer 404. Referring to FIG. 34, the clamp 440'' is substantially the same as the clamp 440 except that in place of a screw, the legs 441, 443 are mechanically clamped together using a compression instrument 20.

Figures 35, 36:
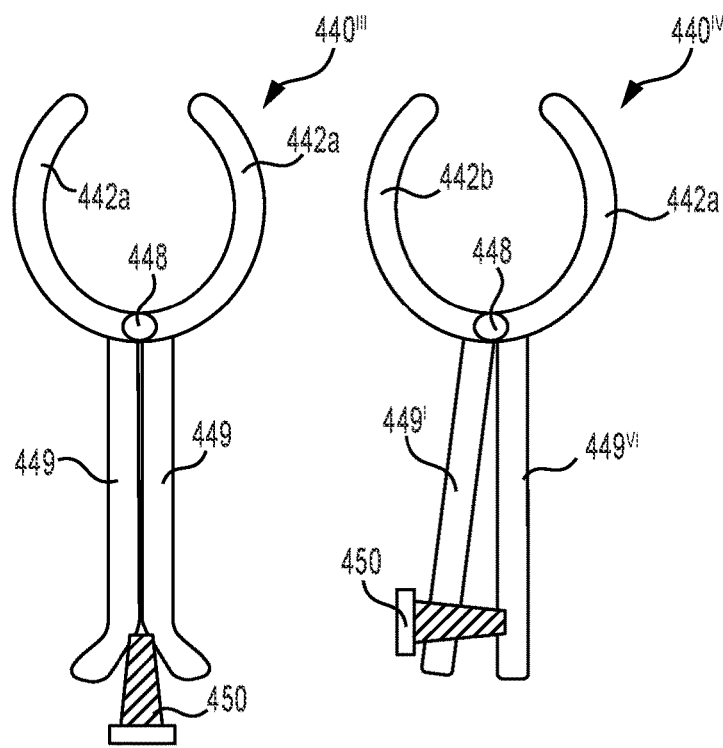
FIG. 35 is a top plan view of another exemplary embodiment of a VBR graft attachment assembly.
FIG. 36 is a top plan view of another exemplary embodiment of a VBR graft attachment assembly.
Figure 37:
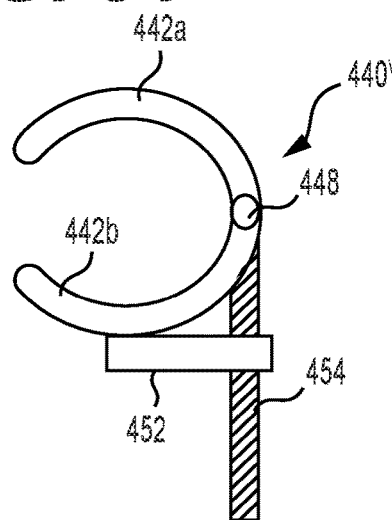
FIG. 37 is a top plan view of another exemplary embodiment of a VBR graft attachment assembly.

Referring to FIGS. 35-37, the clamps 440''', 440$^{iv}$, 440$^{v}$ each include a first and second collar portions 442a, 442b connected to one another via a hinge 448. In the embodiment of FIG. 35, each collar portion 442a, 442b has a leg 449 extending therefrom and a screw 450 is advanced between the legs 449 to splay the legs 449 and thereby bring the collar portions 442a, 442b toward one another. In the embodiment of FIG. 36, the screw 450 extends through one of the legs 449' into contact with the other leg 449'. Advancing of the screw 450 causes one leg 449' to pivot away from the other leg 449', thereby bringing the collar portions 442a, 442b toward one another. In the embodiment of FIG. 37, a closing arm 452 is in contact with one of the collar portions 442b and is engaged by a screw mechanism 454. Rotation of the screw mechanism 454 advances the closing arm 454, thereby bringing the collar portions 442a, 442b toward one another.

Figure 38:
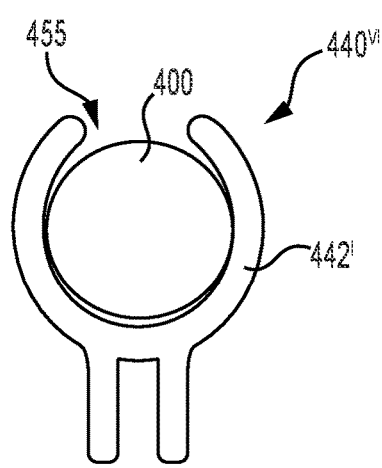
FIG. 38 is a top plan view of another exemplary embodiment of a VBR graft attachment assembly.

Referring to FIG. 38, the clamp 440$^{vi}$ includes a collar portion 442' with an opening 455 into a central area. The opening 455 has a width less than the diameter of the VBR graft 400. The collar portion 442' is manufactured from an elastomeric material such that the collar portion 442' can deform as it is pressed onto the VBR graft 400 and spring into a clamped position when fully attached.

Referring to FIGS. 39-40, the VBR graft 400 is secured within a tulip head 460. In each embodiment, the tulip head 460 includes a body defining a U-shaped VBR receiving area 461. A screw 464, cam or the like is secured in the open end of the body 462, securing the VBR graft 400 within the VBR receiving area 461. In the embodiment of FIG. 39, the stabilizer 404 is attached to the body 462 and in the embodiment of FIG. 40, the stabilizer 404 is attached to the screw 464.

Referring to FIGS. 41-46, the stabilizer 404 is attached to the VBR graft 400 via one or more tethers. In the embodiment of FIG. 41, the tether 470 extends about the outside of the VBR graft 400. The ends 471, 473 are received and secured in the stabilizer 404. In the embodiment of FIG. 42, the tether 470 extends through a hole 417 extending through the VBR graft $404^{vi}$ and the ends 471, 473 are received and secured in the stabilizer 404. In the embodiment illustrated in FIG. 43, the tether 470 extends about the VBR graft 400 and the ends 471, 473 are secured within a buckle 474 attached to the stabilizer 404. In the embodiment illustrated in FIG. 44, the tether 470 extends about the VBR graft 400 and the ends 471, 473 are secured within the stabilizer 404 via a screw 476 extending into the stabilizer 404. In the embodiment illustrated in FIG. 45, the tether 470 extends about the VBR graft and each end is attached to a respective rod 402. In the embodiment illustrated in FIG. 46, a pair of tethers 470a, 470b on opposed sides of the VBR graft 400. Each tether 470a, 470b has one end attached to a portion 408 of one stabilizer 404a and an opposite end attached to a portion 408 of another stabilizer 404b.

In each of the embodiments, the tethers 470 can mate with specific features or no features on the graft and the connection points can be fixed or adjustable. Additionally, the tethers 470 can be left loose or tightened locally or remotely.

Referring to FIGS. 47-50, the stabilizer is attached directly to the VBR graft. In the embodiment illustrated in FIG. 47, the VBR graft $400^{vii}$ includes a threaded bore 480 defined therein. The stabilizer 404' includes at least a portion of external threads 482 configured to threadably engage the threaded bore 480. In the embodiment illustrated in FIG. 48, the VBR graft $400^{viii}$ includes a projection with external threads 484. The stabilizer 404" includes a threaded internal bore 485 configured to threadably receive the threaded projection 484. In the embodiment illustrated in FIG. 49, the VBR graft $400^{ix}$ includes a dovetail projection 486. The stabilizer 404''' includes a dovetail slot 487 configured to receive the dovetail projection 486. In the embodiment illustrated in FIG. 50, the VBR graft $400^x$ includes a through hole 490 extending therethrough. A bolt 492 extends through the through hole 490 and a nut 494 of the stabilizer $404^{iv}$ is tightened onto the bolt 492.

FIGS. 51-63 illustrate components and methods for attaching the stabilizer 404 to the posterior rod 402. In the embodiment illustrated in FIG. 51, the stabilizer 404 is formed integrally with the rod 402. Similarly, in the embodiment illustrated in FIG. 52, the stabilizer 404 is formed integrally with the rod 402', however, the rod 402' has a reinforced section 500 to distribute loads at the junction.

Referring to FIGS. 53-58, the posterior rod 402 includes a collar for attachment of the stabilizer 404. In each of these embodiments, the collar may be formed integrally with the stabilizer 404 or may be manufactured separately and connected relative thereto. In the embodiment of FIG. 53, the collar 502 extends about the rod 402 and includes a through hole 503 through which a set screw 504 extends. Once the collar 502 is positioned as desired, the set screw 504 is advanced into position against the posterior rod 402 to lock the position.

Referring to FIG. 54, the collar 502' extends partially about the posterior rod 402. The orientation of the collar 502' and the stabilizer 404 may be set and thereafter fixed relative to the posterior rod 402 via the set screw 504. In the embodiment illustrated in FIG. 55, the rod 402" includes a section of exterior splines 505. Splines 506 on the inside surface of the collar 502" engage the splines 505 to set the orientation of the collar 502" and stabilizer 404 relative to the posterior rod 402". The embodiment illustrated in FIG. 56 is similar except that the collar 502''' extends completely around the posterior rod 402". In the embodiment illustrated in FIG. 57, the rod 402''' includes at least a portion thereof with exterior threads 507. Threads 508 on the inside surface of the collar $502^{iv}$ engage the threads 507 to set the linear position of the collar $502^{iv}$ and stabilizer 404 relative to the posterior rod 402'''. The embodiment illustrated in FIG. 58 is similar except that the collar $502^v$ extends completely around the posterior rod 402''' such that the collar $502^v$ may be threaded onto the rod 402'''.

Referring to FIGS. 59-60, the posterior rod 402 includes a clamp for attachment of the stabilizer 404. In the embodiment of FIG. 59, the clamp 510 includes a collar portion 512 which extends about the posterior rod 402 to a pair of opposed legs 511, 513. A screw 514 extends through the legs 513, 514. Advancing of the screw 514 brings the legs 511, 513 together, tightening the collar portion 512 about the posterior rod 402. The stabilizer 404 is configured for attachment to the clamp 510. Referring to FIG. 60, the clamp 510' includes a collar portion 512' with an opening 515 into a central area. The opening 515 has a width less than the diameter of the posterior rod 402. The collar portion 512' is manufactured from an elastomeric material such that the collar portion 512' can deform as it is pressed onto the posterior rod 402 and spring into a clamped position when fully attached.

In the embodiment illustrated in FIG. 61, the posterior rod $402^{iv}$ includes a projection 516 with a spherical head 518 and the stabilizer 404' includes a receiving chamber 517 with a complementary spherical configuration. The spherical head 518 is positioned in the receiving chamber 517 and a clamp 519 is affixed about the stabilizer 404' to maintain the head 518 within the chamber 517. The spherical head and chamber allow multiaxial fixation between the rod $402^{iv}$ and the stabilizer 404'.

In the embodiment illustrated in FIG. 62, the posterior rod 402 is secured within a tulip head 520. The tulip head 520 includes a body 522 defining a U-shaped rod receiving area 521. A screw 524, cam or the like is secured in the open end of the body 522, securing the posterior rod 402 within the rod receiving area 521. In the illustrated embodiment, the stabilizer 404 is attached to the body 522.

Figure 44:
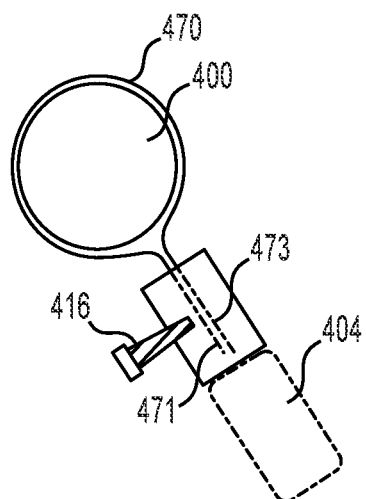
FIG. 44 is a top plan view of another exemplary embodiment of a VBR graft attachment assembly.
Figure 45:
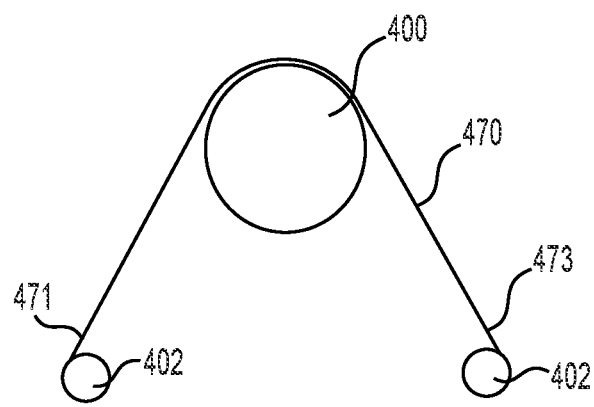
FIG. 45 is a top plan view of another exemplary embodiment of a VBR graft attachment assembly.
Figure 46:
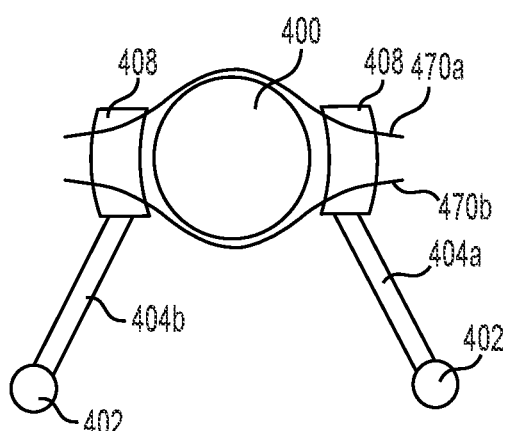
FIG. 46 is a top plan view of another exemplary embodiment of a VBR graft attachment assembly.
Figure 47:
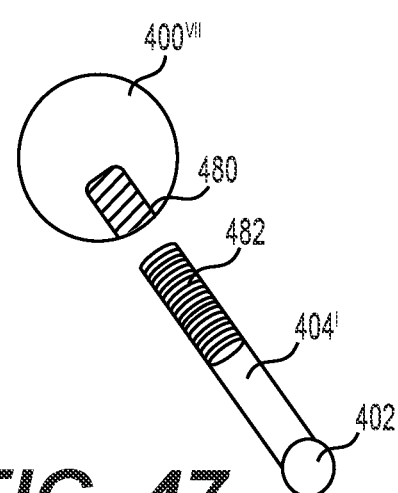
FIG. 47 is an exploded top plan view of another exemplary embodiment of a VBR graft attachment assembly.
Figure 48:
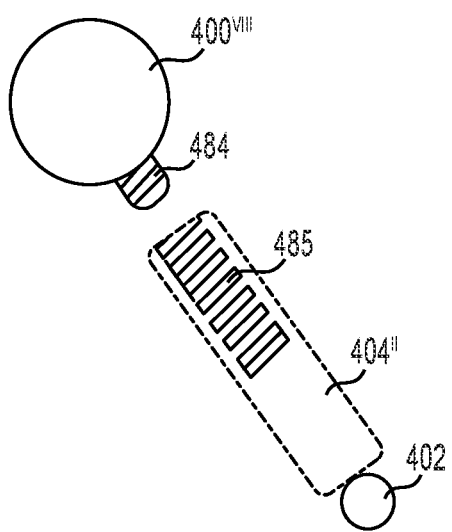
FIG. 48 is an exploded top plan view of another exemplary embodiment of a VBR graft attachment assembly.
Figure 49:
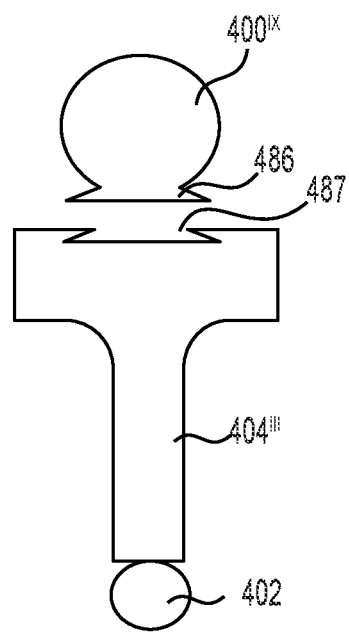
FIG. 49 is an exploded top plan view of another exemplary embodiment of a VBR graft attachment assembly.
Figure 50:
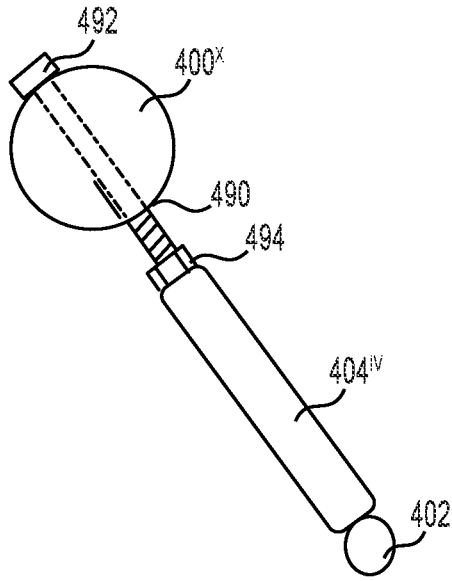
FIG. 50 is a top plan view of another exemplary embodiment of a VBR graft attachment assembly.
Figure 51:
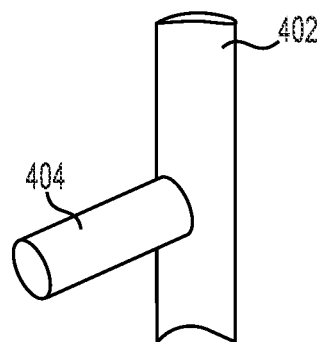
FIG. 51 is an isometric view of an exemplary embodiment of a posterior rod attachment assembly.
Figure 63:
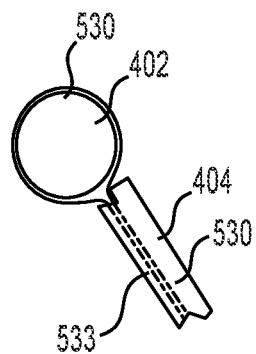
FIG. 63 is a top plan view of another exemplary embodiment of a posterior rod attachment assembly.

Referring to FIG. 63, the stabilizer 404 is attached to the posterior rod 402 via one or more tethers. In the illustrated embodiment, the tether 530 extends about the outside of the posterior rod 42. The ends 531, 533 are received and secured in the stabilizer 404. Tethers may be utilized in other configurations, for example, as illustrated in FIGS. 42-44, to connect the stabilizer 404 and posterior rod 402. In each of the embodiments, the tethers 530 can mate with specific features or no features on the rod and the connection points can be fixed or adjustable. Additionally, the tethers 530 can be left loose or tightened locally or remotely.

Figure 64:
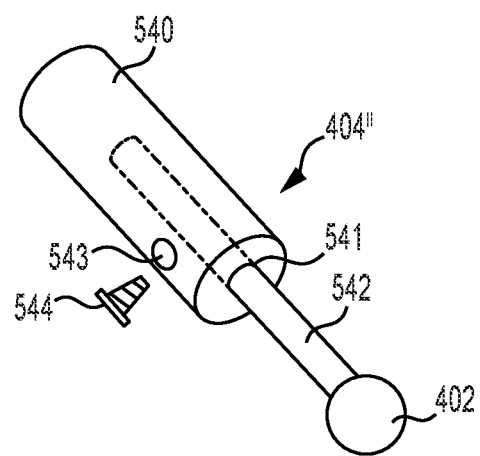
FIG. 64 is an isometric view of an exemplary embodiment of an adjustable stabilizer.
Figure 65:
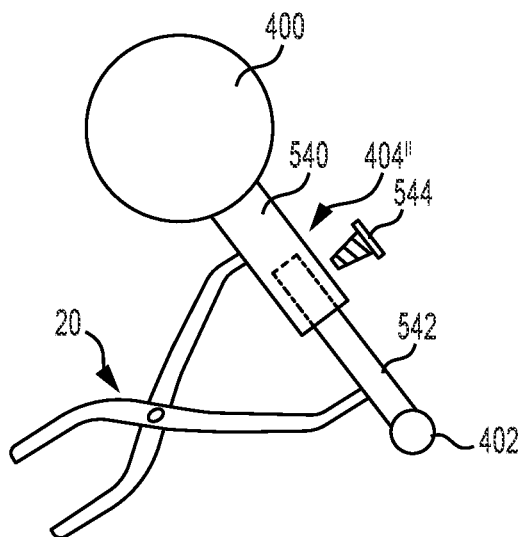
FIG. 65 is an isometric view illustrating adjustment of the length of the adjustable stabilizer of FIG. 64 using a distraction/compression instrument.

FIGS. 64-72 illustrate components and methods for controlling the length of the stabilizer 404 between the VBR graft 400 and the posterior rod 402. Referring to FIGS. 64-65, the stabilizer 404" has a telescoping configuration. The stabilizer 404" includes an outer body 540 with a receiving chamber 541 and an inner body 542 configured to be slidably received in the receiving chamber 541. A set screw 544 extends through a hole 543 in the outer body 540 to lock the position of the inner member 542 once a desired length between the VBR graft 400 and the posterior rod 402 is achieved. As illustrated in FIG. 65, a distraction instrument 20 or the like may engage the outer and inner bodies 540, 542 to adjust the length thereof.

Figure 66:
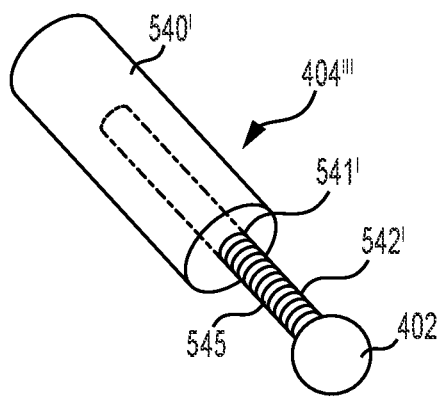
FIG. 66 is an isometric view of another exemplary embodiment of an adjustable stabilizer.

The stabilizer 404''' illustrated in FIG. 66 is similar to that of FIG. 64 and includes an outer body 540' and an inner body 542'. In the present embodiment, the receiving chamber 541' is threaded and the inner body 542' has external threads 545 such that the length may be threadably adjusted.

Figure 67:
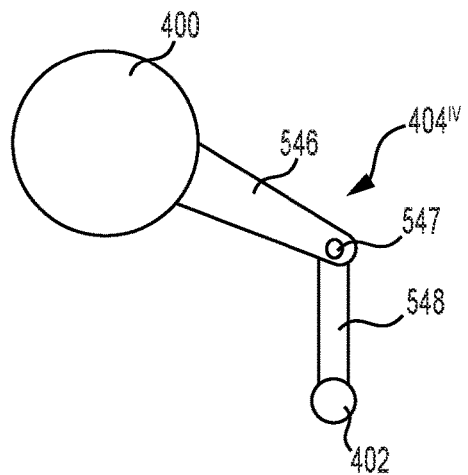
FIG. 67 is a top plan view of another exemplary embodiment of an adjustable stabilizer.

Referring to FIG. 67, the stabilizer 404$^{iv}$ has a hinged configuration. A VBR portion 546 is attached to the VBR graft 400 and a rod portion 548 is attached to the posterior rod 402. A hinge 547 joins the VBR portion 546 and the rod portion 548. The hinge 547 can be locked or articulated/mechanically driven to push the VBR graft 400 and rod 402 apart as well as push them together.

Figure 68:
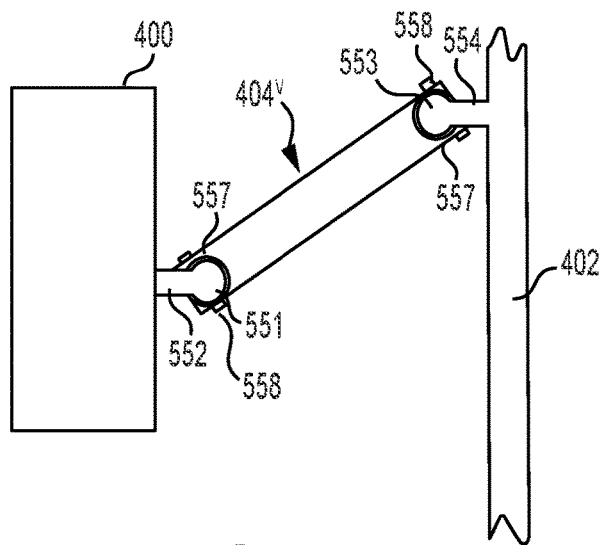
FIG. 68 is a side elevation view of another exemplary embodiment of an adjustable stabilizer.

In the embodiment illustrated in FIG. 68, the stabilizer 404$^v$ provides for multiaxial motion on both ends thereof, however, such multiaxial motion may be provided on only one end. In the illustrated embodiment, a projection 552 with a spherical head 551 extends from the VBR graft 400 and a projection 554 with a spherical head 553 extends from the posterior rod 402. Each end of the stabilizer 404$^v$ includes a spherical receiving chamber 557 configured to receive a respective head 551, 553. A clamp 558 is provided about each end of the stabilizer 404$^v$ to lock the heads 551, 553 within the respective chambers 557. The stabilizer 404$^v$ allows one or both ends of the stabilizer 404$^v$ to be translated along either the VBR graft 400 or the rod 402 and thus allows the stabilizer to fit between the two as the distance between them varies. This design allows for the stabilizer 404$^v$ to push the VBR graft 400 and rod 402 apart as well as push them together.

Figure 69:
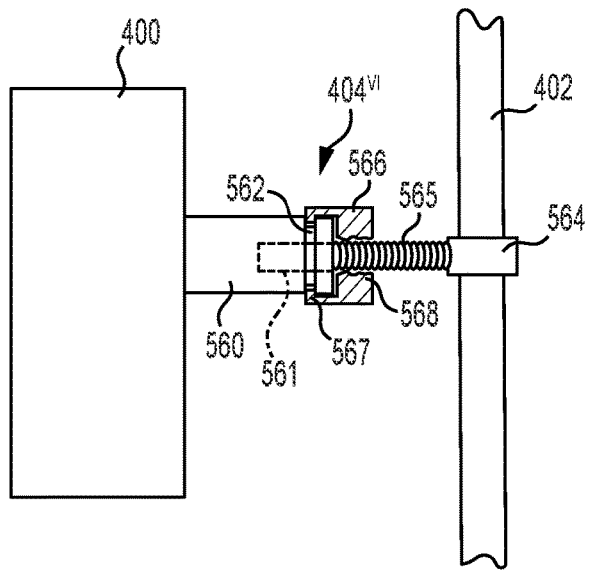
FIG. 69 is a side elevation view of another exemplary embodiment of an adjustable stabilizer.

Referring to FIG. 69, a stabilizer 404$^{vi}$ including a screw jack mechanism will be described. The stabilizer 404$^{vi}$ includes a post 560 extending from the VBR graft 400. The post 560 defines an internal bore 561 and an external groove 562. A post 564 with external threads 565 extends from the posterior rod 402. The post 564 extends into the bore 561. A threaded jack 566 includes a flange 567 which engages the external groove 562 to retain the jack 566 on the post 560 such that the jack 560 is rotatable about the post 560 but does not move axially relative thereto. Threads 568 on the jack 566 engage the threads 565 on post 564 such that rotation of the jack 566 pulls or pushes the post 564 to adjust the position of the rod 402 relative to the VBR graft 400.

In the embodiment of FIG. 70, the stabilizer 404$^{vii}$ includes a shaft 570 with external threads 572. The threaded shaft 570 passively engages an extension 574 on the rod 402, i.e. the shaft 570 rotates relative thereto but does not translate axially. The opposite end of the threaded shaft 570 threadably engages an extension 576 on the VBR graft 400. As the threaded shaft 570 is rotated, the threaded engagement with the extension 576 causes the VBR graft 400 to move toward or away from the posterior rod 402.

Referring to FIGS. 71-72, the stabilizer 404viii is manufactured from a flexible material. Use of a flexible material to connect the VBR graft 400 to the posterior rod 402 allows for compression, extension or both between the two. This design can be combined with any of the above embodiments for a custom fit with the ability to absorb some of the motion between the two components without causing the VBR graft 400 to move.

Although many of the embodiments are described with references to VBR, it will be appreciated that the embodiments may apply equally to an interbody fusion implant where the vertebra or vertebrae are not removed.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A prosthetic implant for engagement between first and second vertebrae comprising:
   a first body including a first plate with a plurality of spaced apart first legs;
   a second body including a second plate with a plurality of spaced apart second legs extending from the second plate, one of the second legs being an expandable leg;
   wherein the first and second bodies are interdigitated such that the first legs extend into the spaces defined between the second legs and the second legs extend into the spaces defined between the first legs; and
   a locking mechanism configured to engage the expandable leg to lock the first body with respect to the second body,
   wherein the locking mechanism includes a cam member.

2. The implant assembly according to claim 1, wherein the locking mechanism includes a tapered screw.

3. The implant assembly according to claim 1, wherein the plurality of first legs are radially spaced from one another to form first spaces.

4. The implant according to claim 3, wherein the plurality of second legs are radially spaced apart to form second spaces.

5. The implant according to claim 1, wherein the expandable leg has a slot.

6. The implant according to claim 5, wherein the slot includes an opening.

7. The implant according to claim 6, wherein the locking mechanism is configured to fit in the opening.

8. The implant according to claim 7, wherein the locking mechanism is a tapered screw.

9. The implant according to claim 1, wherein first body and the second body are configured to be distracted from one another by using an instrument.

10. A method of inserting a prosthetic implant, comprising the steps of:
    providing the prosthetic implant, wherein the prosthetic implant includes:
      a first body including a first plate with a plurality of spaced apart first legs;
      a second body including a second plate with a plurality of spaced apart second legs extending from the second plate, one of the second legs being an expandable leg, wherein the expandable leg has a slot;
      wherein the first and second bodies are interdigitated such that the first legs extend into the spaces defined between the second legs and the second legs extend into the spaces defined between the first legs; and
      a locking mechanism configured to engage the expandable leg to lock the first body with respect to the second body;
    attaching the first body to the first vertebra;
    attaching the second body to the second vertebra;
    engaging the prosthetic implant with an implantation instrument; and distracting or compressing the first body and second body away from or toward one another using the implantation instrument.

11. The method of claim 10, wherein the locking mechanism includes a tapered screw.

12. The method of claim 10, wherein the locking mechanism includes a cam member.

13. The method of claim 10, wherein the plurality of first legs are radially spaced from one another to form first spaces.

14. The method of claim 13, wherein the plurality of second legs are radially spaced apart to form second spaces.

15. The method of claim 10, wherein the slot includes a screw receiving opening.

16. The method of claim 15, wherein the locking mechanism is configured to fit in the screw receiving opening.

17. The method of claim 16, wherein the locking mechanism is a tapered screw.

18. The method of claim 10, wherein first body and the second body are configured to be distracted from one another by using an instrument.

* * * * *